United States Patent [19]

Brunhouse et al.

[11] Patent Number: 5,348,859
[45] Date of Patent: Sep. 20, 1994

[54] METHOD AND APPARATUS FOR OBTAINING AN ABSOLUTE WHITE BLOOD CELL SUBSET COUNT AND WHITE BLOOD CELL MULTIPART DIFFERENTIAL

[75] Inventors: Robert F. Brunhouse, Coral Gables; Constance M. Hajek, Miami Lakes; Thomas Russell, Miami; Wallace H. Coulter, Miami Springs, all of Fla.

[73] Assignee: Coulter Corporation, Miami, Fla.

[21] Appl. No.: 703,163

[22] Filed: May 20, 1991

Related U.S. Application Data

[63] Continuation-in-part of Ser. No. 617,096, Nov. 23, 1990.

[51] Int. Cl.⁵ .................... G01N 33/53; G01N 33/48; G06M 11/02
[52] U.S. Cl. .................... 435/7.24; 435/7.2; 435/7.21; 435/7.23
[58] Field of Search .................... 435/7.2, 7.21, 7.23, 435/7.24

[56] References Cited

U.S. PATENT DOCUMENTS

| | | |
|---|---|---|
| 4,029,470 | 6/1977 | Wilkins et al. |
| 4,115,535 | 9/1978 | Giaever ..................... 535/1 |
| 4,342,739 | 8/1982 | Kakimi et al. ..................... 424/1 |
| 4,483,928 | 11/1984 | Suzuta et al. ..................... 436/519 |
| 4,511,662 | 4/1985 | Baran et al. |
| 4,615,878 | 10/1986 | Kass |
| 4,714,606 | 12/1987 | Kass |
| 4,865,971 | 9/1989 | Kortright et al. ..................... 435/7 |
| 4,931,395 | 6/1990 | Griffin ..................... 435/240.27 |
| 5,006,549 | 4/1991 | Kung et al. ..................... 435/5 |
| 5,061,620 | 10/1991 | Tsukamoto et al. ..................... 435/7.21 |
| 5,068,178 | 11/1991 | Nowinski ..................... 435/7.2 |
| 5,077,216 | 12/1991 | Morganelli et al. ..................... 435/240.27 |

FOREIGN PATENT DOCUMENTS

| | | |
|---|---|---|
| 0157050 | 8/1985 | Japan. |
| 60-157050 | 8/1985 | Japan ..................... 435/7.24 |
| 88/6918 | 9/1988 | PCT Int'l Appl. |
| 2105463 | 3/1983 | United Kingdom. |

OTHER PUBLICATIONS

Caldwell, C. W., et al., 1987, American Journal of Cell Physiology 88(4): 447–456.

Ross, G. D., et al., 1985, The Journal of Immunology, 134(5): 3307–3315.

Brando, U., et al., 1988, Transactions of the American Society for Artificial Internal Organs, 34: 441–441.

Lippi, U., et al., 1990, American Journal of Coagulation Physiology, 93(6): 760–764.

Bauer, J. D., in *Clinical Laboratory Methods*, Ninth Edition, 1982, pp. 178–205. C. V. Mosby Company, publishers.

*Primary Examiner*—Robert A. Wax
*Assistant Examiner*—William W. Moore
*Attorney, Agent, or Firm*—John T. Winburn

[57] ABSTRACT

An optical screening method and apparatus for identifying and counting cells expressing selected characteristics or properties. The cells are combined with one or more different sets of microspheres, each set having a reactant bound thereto which will bind to a specific molecule which can exist on one or more types of the cells. The cells and microspheres are formed in a known volume on a slide and optically viewed to identify and count the type of cells to which the different sets of microspheres do or do not bind. The cell count then is related to the known volume to provide an absolute cell count. A plurality of different sample portions can be utilized with different reactants to obtain a multipart WBC differential/absolute count. The different sets of microspheres are optically differentiated by having different optical characteristics, such as size, shape, color or combinations thereof.

20 Claims, 16 Drawing Sheets

METHOD AND APPARATUS FOR OBTAINING AN ABSOLUTE WHITE BLOOD CELL SUBSET COUNT AND WHITE BLOOD CELL MULTIPART DIFFERENTIAL

CROSS REFERENCE TO RELATED APPLICATION

This application is a continuation-in-part of co-pending U.S. application Ser. No. 617,096, filed Nov. 23, 1990, entitled METHOD AND APPARATUS FOR OPTICALLY SCREENING MICROSCOPIC CELLS, the disclosure of which is incorporated by reference.

BACKGROUND OF THE INVENTION

This invention relates generally to a method and apparatus for identifying or screening cells to obtain an absolute count of the cells and/or a multi-part differential/absolute count for research or diagnostic purposes. More particularly, the invention is directed to optically identifying and counting cells which have specific surface molecules, in a known sample volume to obtain a four part differential and/or the absolute cell count of the population of interest, not previously obtainable by simple optical techniques. Stained cells are the basis of conventional cell morphology study. Typically the cells are placed on a slide, and then stained, where they are optically or visually viewed through a microscope. The optical or visual information from microscopic images also can be utilized in automatic scanning devices such as image analyzers.

In the late 19th century, Ehrlich reported on the morphology, physiology and pathology of blood cells, which advanced hematology into a new era by establishing methods of detecting and differentiating the leukemias and anemias. Ehrlich observed that acidic, basic and neutral dyes react specifically with such cellular components as granules and nuclei of white blood cells (WBC).

Romanowsky continued these advancements in hematology by developing a polychromatic stain for use on cells. Currently, Wright's Stain, a modification of Romanowsky's stain is conventionally utilized to visually examine cells. Peripheral blood smears are stained and routinely visually examined for abnormal morphologic variations. Classification of the types of cells and the stages of cell differentiation are key factors in identifying a disease process. Despite the utilization of automated hematology analyzers and flow cytometry instruments, there remains a need for direct visual (microscopic) evaluation of the cells.

Immunologic studies also are important when anomalies are found on a peripheral blood smear. It is necessary to determine the specific subtype of the leukemia in order to better select a treatment method for the disease and to provide the patient with as specific a prognosis as possible. For example, in forms of acute leukemia, there is a predominance of blasts in the peripheral blood. These immature cells can be difficult to classify as either lymphocytic or granulocytic because of the lack of differentiation. If the blast subpopulation that is rapidly proliferating is found to be T11 receptor bearing, the leukemia can be classified as an acute lymphoblastic leukemia, T-cell type. In general, T lineage ALL has a poorer prognosis than B lineage ALL. Further subgrouping these leukemias according to their level of differentiation is also customary. Groups I and II exhibit antigens that are seen on early thymic precursor cells; while those expressed in Group III are similar to the surface antigens found on mature T cells.

Immunology experiments were first developed utilizing a light microscope for determination of lymphocyte subsets. Rosette formation between human lymphocytes and sheep red blood cells (RBC) was observed by Coombs and others in 1970. Later studies found that all or at least a major portion of thymus-derived lymphocytes (T-cells) under the proper conditions displayed the rosette formation phenomenon. These studies utilized Ficoll isolated lymphocytes and were for a period of time routinely employed for subset classification of isolated lymphocytes utilizing a light microscope.

Lymphocyte subsets now conventionally are determined by fluorescent labeling of the cells, in a sample with a fluorescent-tagged monoclonal antibody. The fluorescent-tagged monoclonal antibody binds to the antigen of interest on the surface of the cells expressing the antigen. The cell sample then is analyzed by utilizing a fluorescent microscope or by utilizing a highly sophisticated flow cytometry instrument. When utilizing a flow cytometry instrument, the cell sample preparation, data collection and data analysis must be performed by a specially trained technician. The flow cytometry instrument includes a laser and complex optical system, a high-power computer and electrical and fluidic systems. The component systems of the flow cytometry instrument must be properly maintained and calibrated on a regular and frequent basis. Although the flow cytometry instrument currently is the reference lymphocyte subset determination method, the method has several drawbacks including the high cost of the instrument and the expertise required to correctly operate such instrument.

Lymphocyte subsets also can be determined utilizing automated instruments and methods developed by the assignee of the present application, Coulter Electronics, Inc. An improved simple automated instrument and methods of using the same is disclosed in U.S. application Ser. No. 587,646, filed Sep. 20, 1990, entitled AUTOMATED ANALYZER AND METHOD FOR SCREENING CELLS OR FORMED BODIES FOR ENUMERATION OF POPULATIONS EXPRESSING SELECTED CHARACTERISTICS, which is a continuation of U.S. Ser. No. 025,345, filed Mar. 13, 1987 of the same title. This application combines the application of electronic sensing aperture principles, the specificity of selected biological molecules for identifying and/or enumerating defined populations of cells or formed bodies and microscopic particle technology. The automated analyzer can be used together with a special lysing reagent and/or antibodies coupled to microscopic microspheres or supports of varying composition.

A second application, U.S. Ser. No. 07/849,481, filed Mar. 10, 1992, now issued as U.S. Pat. No. 5,223,398, which is a continuation of U.S. Ser. No. 285,856, filed Dec. 16, 1988, now issued as U.S. Pat. No. 5,231,005, entitled METHOD AND APPARATUS FOR SCREENING CELLS OR FORMED BODIES WITH POPULATIONS EXPRESSING SELECTED CHARACTERISTICS, discloses the screening of direct subsets from whole blood samples or portions thereof.

A third application, U.S. Ser. No. 07/929,156 filed Aug. 12, 1992, now issued as U.S. Pat. No. 5,260,192, which is a continuation of U.S. Ser. No. 339,156, filed Apr. 14, 1989, entitled METHOD AND APPARATUS FOR SCREENING CELLS OR FORMED BODIES WITH POPULATIONS EXPRESSING SELECTED CHARACTERISTICS UTILIZING AT LEAST ONE SENSING PARAMETER, discloses multipart or five part white blood cell differentials, lymphocyte subsets and overlapping determinations performed from a whole blood sample or from a sample with the red blood cells and/or populations of the white blood cells removed by elimination of populations and/or subsets thereof with one or more light or electronic parameters.

A fourth application, U.S. Ser. No. 07/525,231, filed May 17, 1990, entitled METHOD AND APPARATUS FOR SCREENING OBSCURED OR PARTIALLY OBSCURED CELLS, discloses an analysis of obscured cells by utilizing microspheres having specific monoclonal antibodies bound thereto to move the sensed characteristics of the obscured cells from one cell population to another. Each of the above four referenced applications is incorporated herein by reference.

The method and apparatus embodying the invention can be utilized with a variety of immunological reactions, such as immunological reactions involving reactants and formed bodies or cells. The invention also applies to analyses of formed body suspensions such as some bacteria and viruses among others. As utilized herein, cells are defined as animal or plant cells, including cellular bacteria, fungi, which are identifiable separately or in aggregates. Cells are the least structural aggregate of living matter capable of functioning as an independent unit. For example, cells can be human red blood cell (RBC) and WBC populations, cancer or other abnormal cells from tissue or from blood samples. Formed bodies are defined as some bacteria and viruses. The cells and formed bodies suitably tagged or labeled, reasonably can be expected to be optically identified by the method and apparatus of the invention in the same manner as the human blood cell examples.

Although the term "reactant" has been utilized in the above applications to define lysing agents and monoclonal antibodies, reactants can include various agents which detect and react with one or more specific molecules which are on the surface of a cell or formed body. Some examples are given below:

| Reactant | Specific Molecule |
|---|---|
| Antibody | Antigen |
| Drug | Drug Receptor |
| Hormone | Hormone Receptor |
| Growth Factor | Growth Factor Receptor |

The reactants couple or bind to the specific molecule(s) on the cells. These reactants do form part of a chemical reaction; however, the reactants are not necessarily chemically altered.

One prior art procedure of lymphocyte subset determination utilizes a light microscope and antibody-labeled microspheres. This procedure is available from Bio-Rad Laboratories of Richmond, Calif. The procedure is available to identify T and B lymphocytes. The antibody-labeled microspheres are utilized to bind to the cells which exhibit the surface antigen of interest. Two different colored antibody-labeled microspheres are utilized to differentiate the T and B lymphocytes. The microscopist identifies the cells positive for a particular antigen by the presence of the antibody-labeled microspheres bound to the cells. Cells which do not have an antibody-labeled microsphere bound thereto represent the negative cell population, not expressing the antigen(s) of interest. This procedure is limited by the fact that the lymphocytes must first be isolated from a whole blood sample, utilizing an isolation medium, such as Ficoll-Hypaque. Granulocyte contamination can lead to falsely elevated non-positive cell values and an increased number of phagocytic cells. Further, only lymphocyte subset determinations can be performed, since the remaining cells from a whole blood sample first are eliminated. Also, the cell morphologic evaluation is limited since the cells are not stained with the conventional Romanowsky or Wright type stain, but merely are stained to determine the cell viability. The morphologic evaluation is further limited since the cells are evaluated in a suspension and are not evaluated on slides, as is conventional.

An improved method and apparatus for optically screening cells to identify the morphology and selected characteristics or properties expressed by the cells is disclosed in parent application U.S. Ser. No. 617,096, filed Nov. 23, 1990 entitled METHOD AND APPARATUS FOR OPTICALLY SCREENING MICROSCOPIC CELLS, incorporated herein by reference. The cells are combined with one or a plurality of different sets of microspheres, each set having a reactant bound thereto which will bind to a specific molecule which can exist on one or more types of the cells. The cells and microspheres are prepared as a smear on a slide and stained with a Wright type stain. The cells then are optically viewed by an operator and/or automatically, to identify the type of cells, if any, to which the different microspheres are bound.

SUMMARY OF THE INVENTION

The invention provides a method and apparatus for optically screening cells to identify and count cells of interest in a known sample volume to obtain an absolute cell count and/or a multi-part differential/absolute count. The cells are combined with one or a plurality of different sets of microspheres, each set having a reactant bound thereto which will bind to a specific molecule which can exist on one or more types of the cells.

Following mixing and combining the sample portion with the set or sets of microspheres, the sample portion is lysed to remove the red blood cells. A specific volume of the lysed sample portion then is placed onto a slide, such as a hemacytometer, with or without quenching of the lyse. The cells then are optically viewed by an operator and/or automatically, to identify and count the type of cells, if any, to which the different microspheres are bound. The cell count then is related to the known specific volume to provide an absolute cell count.

The total WBC count also can be obtained, as in the prior art, and then separate sample portions can be combined with one or more sets of microspheres to differentiate different WBC subsets. Each of the different WBC subsets also are optically viewed and counted. The separate sample portion counts then are compared to one another and to the total WBC count to obtain at least a four part WBC differential/absolute count of M's, L's, N's and E's.

The sample can be a whole blood sample or portion thereof and the RBC's are removed from the sample. A second set of different microspheres can be added to differentiate between types of cells if a particular specific molecule, such as an antigen, exists on more than one type of cell. The sets of microspheres can be combined separately and sequentially or concurrently in the same sample portion and preferably are mixed therewith. The different sets of microspheres have different optical characteristics to be optically differentiated. The different optical characteristics between the sets can be color, size, shape or a combination thereof.

BRIEF DESCRIPTION OF THE DRAWINGS

FIG. 1 is a schematic block diagram of one optical screening analyzer embodiment of the present invention;

FIG. 2 is a schematic block diagram of a second optical screening analyzer embodiment of the present invention;

FIG. 3 is a block diagram of a specific optical screening analyzer embodiment of the present invention;

FIG. 4 is a drawing of an optical image of a stained slide illustrating the binding of microspheres to a specific cell antigen;

FIG. 5 is a drawing of an optical image of a stained slide illustrating the binding of microspheres to a different specific cell antigen;

FIG. 6 is a drawing of an optical image of a stained slide illustrating the binding of microspheres to a further different specific cell antigen indicating the type of CLL;

FIG. 7 is a drawing of an optical image of a stained slide illustrating the non-binding of microspheres to another specific cell antigen, further differentiating the type of CLL;

FIG. 8 is a drawing of an optical image of a stained slide illustrating the binding of microspheres to a specific cell antigen on a neutrophil;

FIG. 9 is a drawing of an optical image of different colored microspheres illustrating the binding of microspheres to another specific cell antigen on neutrophils;

FIG. 10 is a drawing of an optical image of both the different colored and different sized microspheres of FIGS. 8 and 9 illustrating the binding of different microspheres to different cell antigens on neutrophils;

FIG. 11 is a drawing of an optical image of the binding of microspheres to a specific cell antigen on one type of cell and the non-binding to antigens on other types of cells;

FIG. 12 is a drawing of an optical image of a stained slide illustrating the binding of microspheres to a different specific cell antigen on one type of cells and the non-binding to antigens on other types of cells;

FIG. 13 is a drawing of an optical image of a stained slide illustrating the binding of microspheres having a second reactant bound thereto bound to a first reactant which binds to a specific cell antigen on the cells;

FIG. 14 is a drawing of an optical image of a stained slide illustrating the binding of microspheres to a specific cell antigen on a neutrophil in bone marrow;

FIG. 15 is a schematic block diagram of one optical cell counting embodiment of the present invention;

FIG. 17 is a drawing of an optical image of a portion of a hemacytometer illustrating the binding of microspheres to a specific cell antigen on lymphocytes; and FIG. 18 is a drawing of an optical image of a portion of a hemacytometer illustrating the binding of different microspheres to a specific cell antigen on each of the lymphocytes and monocytes.

DETAILED DESCRIPTION OF THE PREFERRED EMBODIMENTS

FIGS. 1–14 describe the embodiments disclosed in the parent application Ser. No. 617,096.

Figure 1:
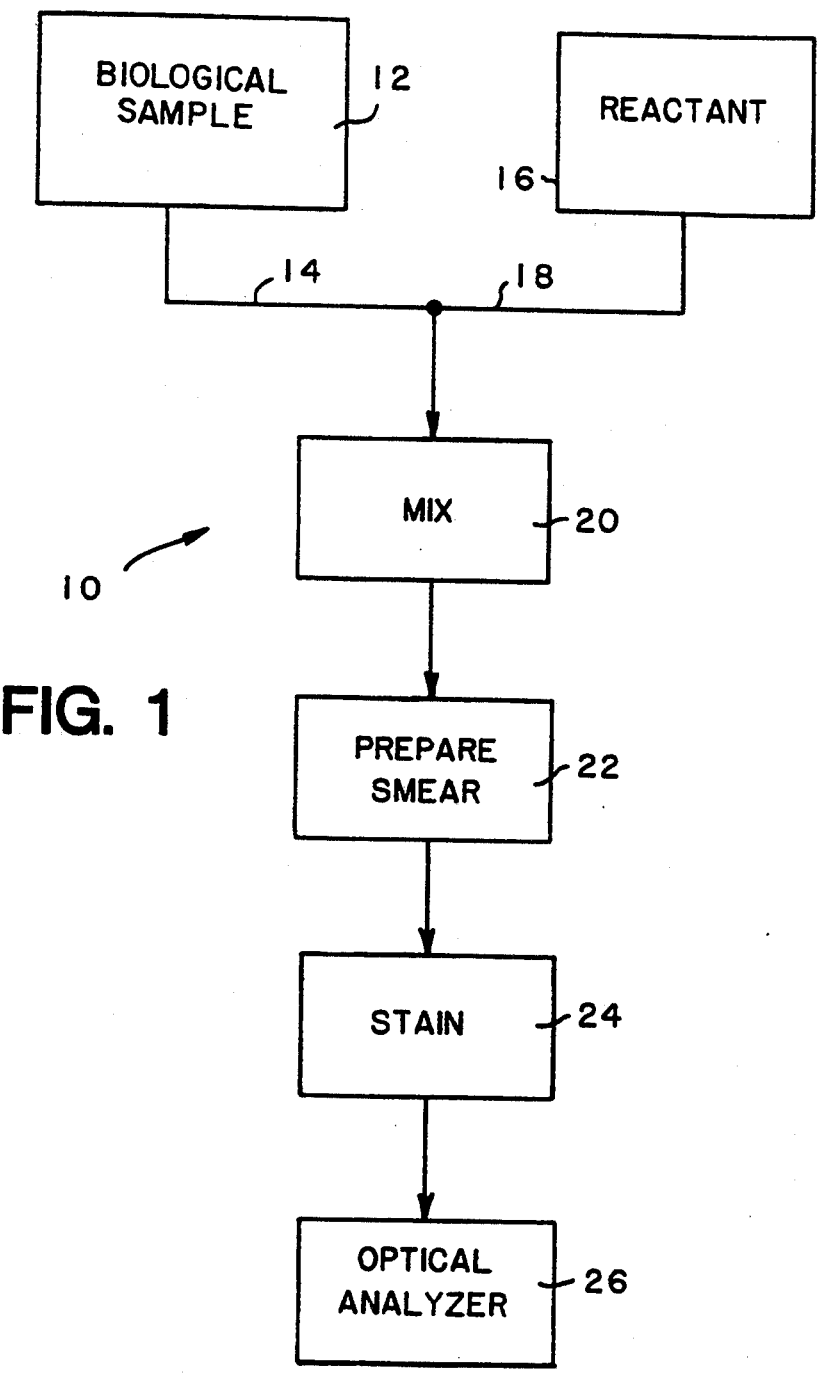
FIGS. 1–14 describe the embodiments disclosed in the parent application Ser. No. 617,096.
Figure 2:
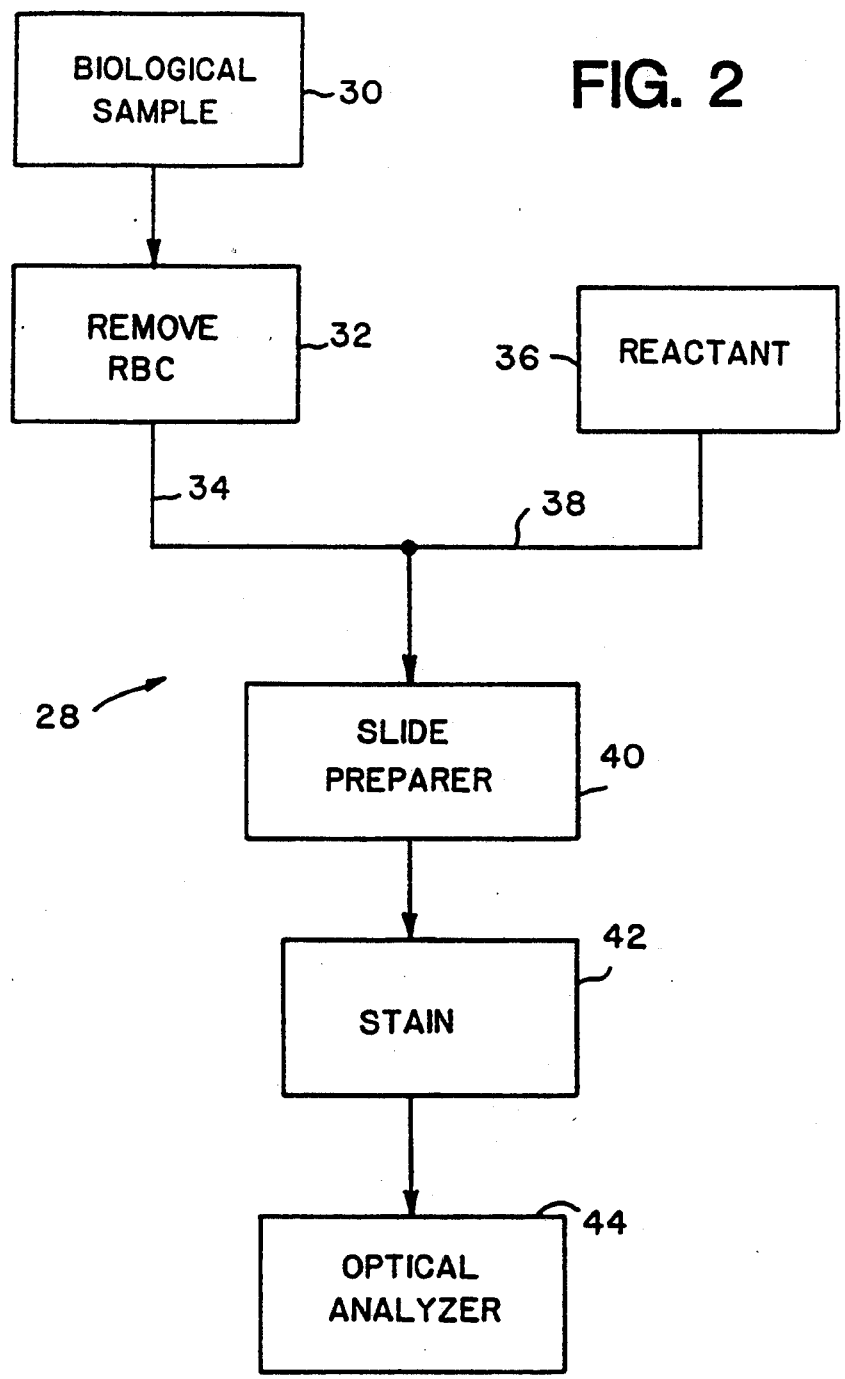

Referring to FIG. 1, a first optical cell screening embodiment of the present invention, is designated generally by the reference character 10. The optical cell screener 10 includes a biological sample 12, which contains at least a first set of biological cells (not illustrated), such as in or from a whole blood sample.

The sample 12 is combined via a line 14 with at least one reactant 16 via a line 18. The reactant 16 can include a chelating agent, such as standard EDTA added to the sample 12 as a blood anticoagulating agent and to prevent the neutrophils (N's) from ingesting the microspheres.

The reactant 16 also includes a plurality or first set of microspheres, having an antibody specific to a particular antigen which can exist on at least one type of cell bound thereto. For blood, the cells express antigens to which a specific antibody or antibodies will bind. In general, antigens are molecules as are the antibodies which will bind thereto, and therefor for blood or other viable cells, the reaction can be specified as a first type of molecule which chemically interacts specifically with a second type of molecule. The combined sample 12 and the reactant 16 then preferably are mixed by a functionally designated mixing station 20. A portion of the mixture then is placed on a slide and a smear is prepared therefrom by a functionally designated smear preparing station 22. The smear then is stained in a functionally designated staining station 24.

The stain should be one of the groups of histological stains, which are utilized to differentiate various cell characteristics. For blood cells, the stain preferably is a so-called "Wright" type stain, as previously described, the stain allows the morphology of the cells to be differentiated under a microscope in a conventional matter. Some other types of histological stain examples useful in the procedures of the present inventions are Hematoxylin, Gentian Violet and Giemsa Blood Stain. Hematoxylin is utilized as a general tissue stain for animal histology designed to show nuclei. Gentian Violet is utilized as a bacterial stain designed to show capsules. Giemsa Blood Stain is utilized to show differentiation of types of leukocytes, rickettsiae, bacteria and inclusion bodies. The stained slide then is optically viewed at an optical analyzer 26. The cells on the slide are optically screened to determine which types of cells have the microspheres bound thereto. This identifies the presence or absence of specified receptors or antigens on the cells and hence the status of the sample, as will be further described hereinafter.

In the optical screening instrument 10, the sample 12 is either a whole blood sample and the red blood cells (RBC's) are left therein or the sample 12 is only a portion of a whole blood sample which may or may not include platelets or RBC's and all the WBC populations. A second optical cell screener embodiment of the present invention is designated generally by the reference character 28, referring to FIG. 2. The optical cell screener 28 includes a biological sample 30, which can be a whole blood sample or can be a blood sample at least including WBC's. The biological sample 30 also can be derived from other biological fluids, such as bone marrow, urine, spinal or pleural fluids.

The RBC's can be removed from the mixture by a functionally designated RBC removing station 32, when desired. The RBC's can be removed from the mixture by the station 32 in a number of ways. The RBC's can be lysed by a lyse. One such preferential lyse and a quench which can be utilized therewith is described hereinafter. The RBC's also can be removed utilizing a plurality of magnetic microspheres with an antibody specific to the RBC's bound to the microspheres (not illustrated). The bound RBC's are held in a magnetic field, while the remaining sample is removed to remove the RBC's. For example, one particular RBC specific antibody which can be utilized is disclosed in U.S. Pat. No. 4,752,563, entitled MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY, which is incorporated herein by reference. A buffer can be included in addition to or in place of the sample buffer. A combination of the preferential RBC lyse and the RBC specific microspheres also can be utilized. Details of the RBC removal can be found in the four incorporated instrument applications of the assignee of the present invention, cited on pages 3 and 4 herein.

The sample 30 then is combined via a line 34 with a reactant 36 via a line 38. The combined sample 30 and reactant 32, preferably are mixed together. Specific details of an appropriate mixing apparatus which can be utilized herein are disclosed in Ser. No. 517,309, filed May 1, 1990, now issued as U.S. Pat. No. 5,238,812, entitled METHOD AND APPARATUS FOR RAPID MIXING OF SMALL VOLUMES FOR ENHANCING BIOLOGICAL REACTIONS, which is a continuation of Ser. No. 025,337, filed Mar. 13, 1987 of the same title, which are incorporated herein by reference. By utilizing the mixer the reactions can be enhanced in speed without significantly damaging the properties of interest of the cells, if desired. The mixer 20 could utilize the same type of mixing apparatus, but also can be other types of gentle mixing apparatus, such as a simple roller rocker, since reaction speed is not necessarily critical.

A portion of the RBC removed mixture then is concentrated as a smear on a slide by a slide preparing station 40. Once the slide is prepared by concentrating the cells of interest and removing the excess moisture, such as by slide centrifugation, the slide is stained as before in a stain station 42. The stained slide then again is optically analyzed by an analyzer 44, which can be the same as the analyzer 26.

The optical cell screener 28 has been described with the removal of the RBC's prior to mixing with the reactant 36. In general this is preferable for use when removing the RBC's with magnetic microspheres. This also allows fewer microspheres of interest to be utilized, since the RBC's are removed and cannot interfere with the binding of the microspheres. When utilizing lyse, it is preferable to remove the RBC's after the reactant 36 and sample 30 are combined, so that the cells are exposed to the lyse for a shorter period of time.

Figure 3:
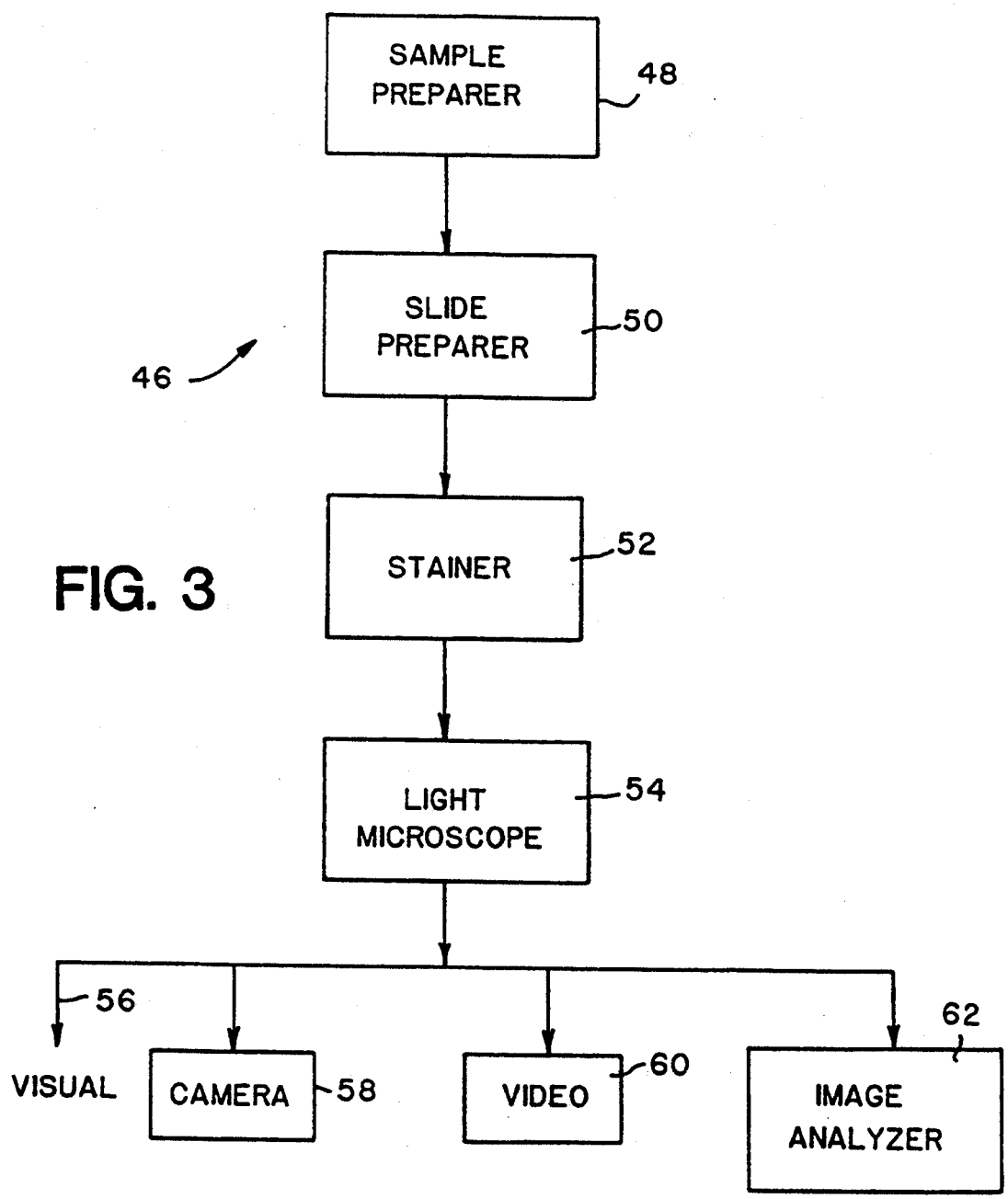

An automated or semi-automated optical cell screener embodiment is illustrated in FIG. 3, designated generally by the reference character 46. The optical cell screener 46 includes a sample preparer 48, which can eliminate RBC's or platelets if desired and add one or more different sets of microspheres with different antibodies bound thereto, which are specific to different antigens which can exist on one or more types of cells in the sample. The sample preparer 48 preferably also will combine and preferably will mix the sample and microspheres to provide rapid binding of the cells and microspheres.

An aliquot or portion of the prepared sample then is formed as a smear on a slide by a slide preparer 50. The slide preparer 50 can be either a conventional slide preparer of a slide containing the RBC's or a slide spinner for a sample with the RBC's removed.

The slide then is stained in a stainer 52. Once the slide is stained, the sample can be optically viewed or analyzed utilizing a light microscope 54. The light microscope 54 can have numerous outputs, a visual output 56 for a user's eyes, a camera output 58 for taking photographs of the cells and microspheres, a video output 60 which can be viewed by users other than the user of the visual output 56 and from which scanning tapes can be made and an image analyzer output 62, which automatically can scan and identify both the morphology of the cells and the color and/or size of the microspheres. Numerous types of conventional image analyzers can be utilized, such as those sold by Inovision Corp. Research Triangle Park, North Carolina, and the Bio Vision workstation sold by Perceptics Corporation, Knoxville, Tenn.

Each biological sample contains at least a first set of biological cells (not illustrated), including at least one white blood cell population having at least one definable subset, such as in or from a whole blood sample. As utilized herein, WBC subsets are subsets of a WBC population to which specific monoclonal antibodies can be bound. A nomenclature now has been defined for the monoclonal antibodies by the World Health Organization and the International Immunology Society. The monoclonal antibodies are defined by a cluster designation (CD) nomenclature which defines a particular specificity for a cell or group of cells and the monoclonal antibodies specific for that CD group. For example purposes only, seven CD groups have been utilized in the following examples, CD2, CD4, CD8, CD10, CD20, CD29 and CD34. The CD nomenclature, specificity and some commercial sources of monoclonal antibodies are illustrated in Table I.

TABLE I

| Cluster of Differentiation | Antibody (Commercial Source)[b] | Specificity |
| --- | --- | --- |
| CD2(gp 50)[a] | T11 (Coulter) OKT11 (Ortho); Leu5a (BD) | E Rossette Receptor |
| CD4(gp 56) | T4 (Coulter) OKT4$_a$ (Ortho);Leu3a (BD) | Helper/inducer T |
| CD8(gp 32-33) | T8 (Coulter) OKT8 (Ortho);Leu2a (BD) | Cytotoxic/ Suppressor T |
| CD10(gp100) | J5 (Coulter) Anti-CALLA (BD) | Common Acute Lymphoblastic Leukemia Antigen pre-B cells, granulocytes |
| CD14(gp 55) | MO2, MY4 (Coulter) | Monocytes, few granulocytes |
| CD20(gp 35) | B1 (Coulter) Leu 16 (BD) | All B cells except for plasma |

TABLE I-continued

| Cluster of Differentiation | Antibody (Commercial Source)[b] | Specificity |
| --- | --- | --- |
| | | cells, B cell tumors, except for myeloma, some non-T ALL cells |
| Cdw29(gp135) | 4B4 (Coulter) | Helper/inducer T |
| CD34(gp115) | HPCA-1 (BD) | Myeloid progenitors |
| CD41 (p130,115)[c] | PLT-1 (Coulter) | Platelets and megakaryocytes |

[a] gp - glycoprotein, molecular weight in kilodaltons
[b] Coulter - Coulter Immunology Division of Coulter Corporation (Hialeah, Florida)
BD - Becton-Dickinson Immunocytometry Systems
Ortho - Ortho Diagnostic Systems (Raritan, New Jersey)
[c] p - protein, molecular weight in kilodaltons Additionally, two other antibodies are utilized for example purposes, which do not yet have CD nomenclatures. One antibody is an N specific antibody disclosed in U.S. Pat. No. 4,931,395, entitled MONOCLONAL ANTIBODY SPECIFIC TO NEUTROPHILS, so-called "1D3". The second antibody is an N and E specific antibody disclosed in U.S. Pat. No. 4,865,971, entitled MONOCLONAL ANTIBODY SPECIFIC TO A COMMON DETERMINANT SITE OF NEUTROPHILS AND EOSINOPHILS, so-called "KC-48" both of which are incorporated herein by reference.

The magnetic microspheres utilized can be of any suitable type and in the examples are polystyrene magnetic microspheres of 0.7 and 1.3 micron diameter, with a weight to volume of 10% solids, sold by Bangs Laboratories of Carmel, Ind. The non-magnetic microspheres again can be of any suitable type and in the examples are surfactant free sulfated polystyrene latex microspheres of 1.05, 2.17 and 3.06 micron diameter with a weight to volume of 8% solids, sold as IDC microspheres by Interfacial Dynamics of Portland, Oreg.

Although these specific microspheres are utilized for example purposes, other types and sizes of microspheres from other conventional sources also can be utilized. In general it is preferable to utilize microspheres of a 5 micron diameter or less, since it is preferable to have a plurality of the microspheres to bind to each cell. Also, the slide and morphology of the cells are better maintained with smaller size microspheres. However, larger diameter microspheres can be utilized and a 10 micron diameter non-magnetic microsphere has been utilized. In this case, however, a plurality of cells will bind to each microsphere rather than vice versa.

It appears that the specificity of the procedure of the present invention is sufficiently specific that a single microsphere is indicative that the antigen/receptor is present on the cell. However, to eliminate potential false readings due to coincidence, only cells binding two or more microspheres are deemed to be indicative of the receptor being present. Generally, depending upon the number/concentration of microspheres, more than one microsphere will bind to each cell exhibiting the specified antigen/receptor.

In general, the procedure is as follows:

1. Add well mixed whole blood to an EDTA tube (i.e. one already containing EDTA), if not collected in EDTA. It is preferred that the blood be collected in EDTA.

2. Add 100 ul of the blood from the EDTA tube to a test tube.

3. Add appropriate microsphere volume[1] to the blood and vortex mixture for approximately 2-3 seconds.

4. Cap the test tube and gently mix for a time sufficient to bind the cells to the microspheres. Times on the order of ten minutes have been found to be sufficient.

5. Following mixing, withdraw an aliquot and make a blood smear. The smear should resemble a peripheral blood smear commonly used for counting differentials.

6. When the slides have dried thoroughly, stain with Wright or Wright/Giemsa stain using the same procedure as for conventional differential slides.

7. View the slide on an immersion oil lens using a 40 x or 100 x objective noting the cells which have the microspheres attached to them.

8. Qualitative positive results are seen when a specific cell type is consistently tagged with two or more microspheres. The degree of positivity of a cell population for a particular antigen can be reflected in the number of cells of that population which are bound by microspheres.

| [1] Suggested microsphere to whole blood ratio according to total white cell count is as follows: | |
| --- | --- |
| WBC ct (cells/ul) | Bead Volume (1% reagent soln of 2.17 micron microspheres) |
| 0–20,000 | 10 ul |
| 20,001–75,000 | 20 ul |
| more than 75,000 | 30 ul |

Reagent consists of a 1% solution of 2 um latex particles in 1.0% bovine serum albumin, 0.1% sodium azide and phosphate buffered saline solution.

If it is desired to deplete the platelets, then the following procedure is utilized to deplete the platelets prior to adding the blood to the test tube in step 2 above.

1. Add 200 microliters EDTA anticoagulated whole blood to a test tube.

2. Add 20 microliters of magnetic PLT-1 microspheres.

3. Mix for a time sufficient to bind the cells to the microspheres. Times of 15 seconds to 2 minutes have been found to be sufficient.

4. Place in magnetic field for 5 minutes.

5. Remove supernatant (whole blood minus microspheres with attached platelets).

6. Use in above procedure at stage 2.

Figure 4:
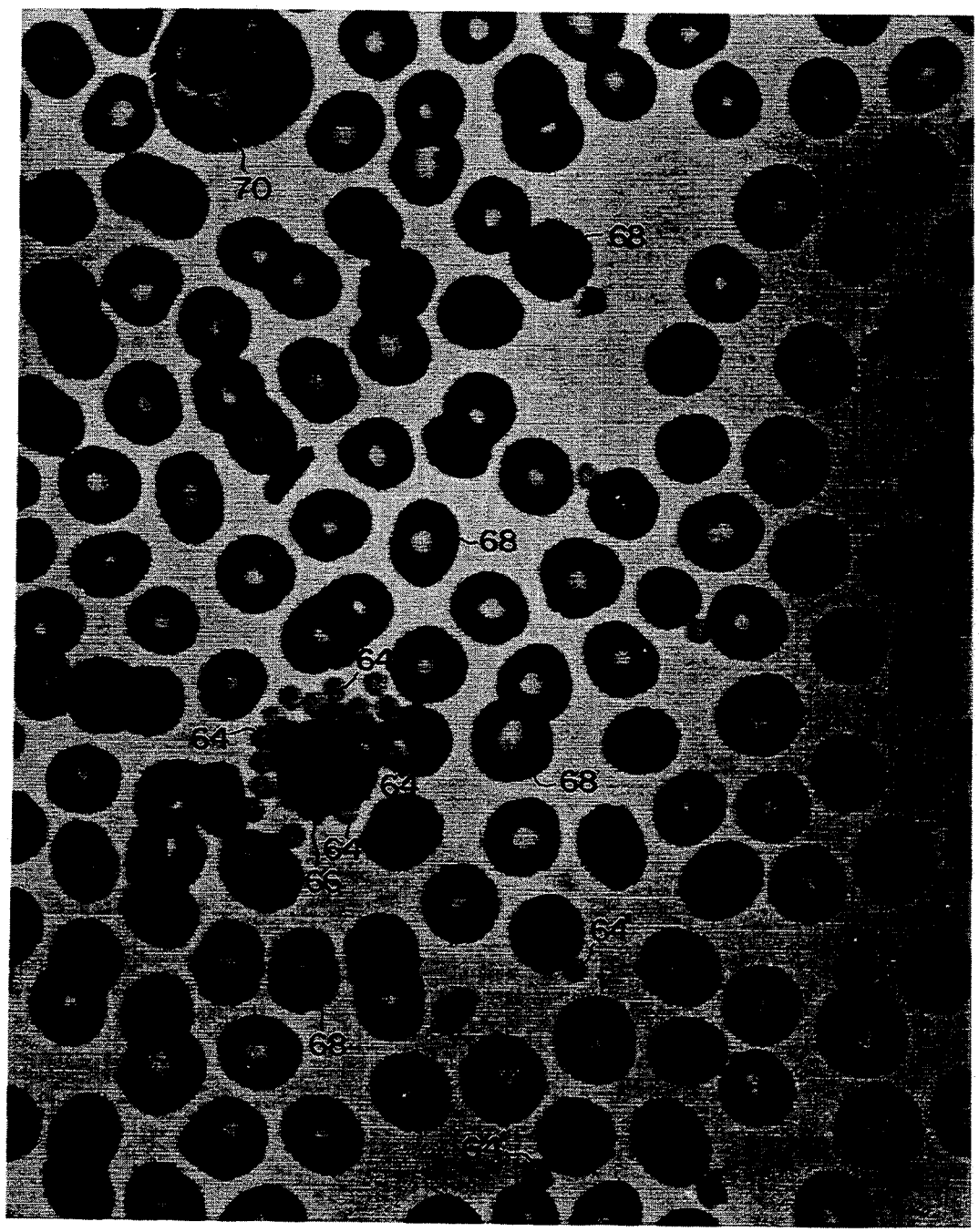

Utilizing the procedure of the invention, the specificity of CD2 to lymphocytes is illustrated in FIG. 4. A plurality of non-magnetic microspheres 64 having a T11 specific antibody bound thereto are shown bound to a lymphocyte cell 66 on a slide in which the RBC's 68 have not been removed. There are some free (non-bound) T11 microspheres 64'. A neutrophil 70 illustrates the specificity of the T11 microspheres 64, since they do not bind to the neutrophils 70.

The drawings are depicted in black and white in accordance with standard drawing conventions, however, the actual stained slides are in color. In that regard, as is conventional, the various cells are colored as follows:

Neutrophils: Cytoplasm is light pink and the small, numerous granules have a light pink to bluish-black color. The nucleus is dark bluish-purple.

Blasts: Bluish cytoplasm which stains unevenly and nucleus is purple.

Lymphocytes: Cytoplasm is blue, and the nucleus is dark bluish-purple.

Eosinophils: Cytoplasm is obscured by the large spherical granules which stain reddish-orange. The nucleus is dark bluish-purple.

Monocytes: Cytoplasm is grey-blue and the nucleus is dark bluish-purple.

Basophils: Granules are dark purple and nucleus is slightly lighter colored. Granules obscure the cytoplasm.

Red Blood Cells: Cells are red but color is less intense in the middle.

Platelets: Cells are light blue with small bluish granules.

In addition, the magnetic type microspheres are reddish-brown and the non-magnetic microspheres are white. This allows the cells and microspheres to easily be differentiated from one another. The microspheres also can be other colors, sizes and shapes to provide the differentiation, as desired.

Figure 5:
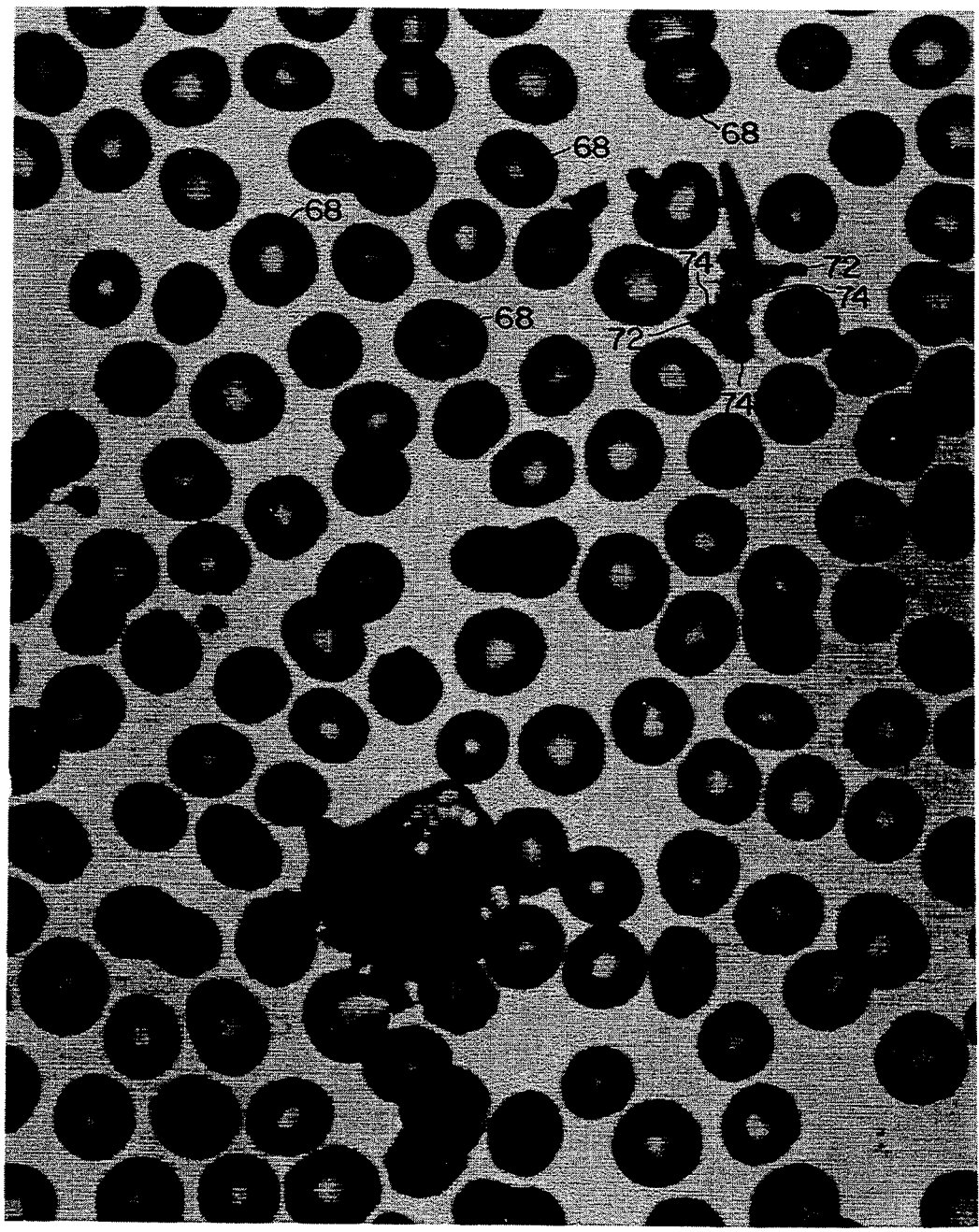

Referring to FIG. 5, a plurality of non-magnetic microspheres 72 having a 4B4 specific antibody bound thereto are shown bound to a plurality of platelets 74, which appear to have been clumped together by the microspheres 72. Since the 4B4 specific antibody binds to platelets as illustrated and will also bind to some L's, the platelets are first depleted prior to analyzing a sample for 4B4 type L's.

Figure 6:
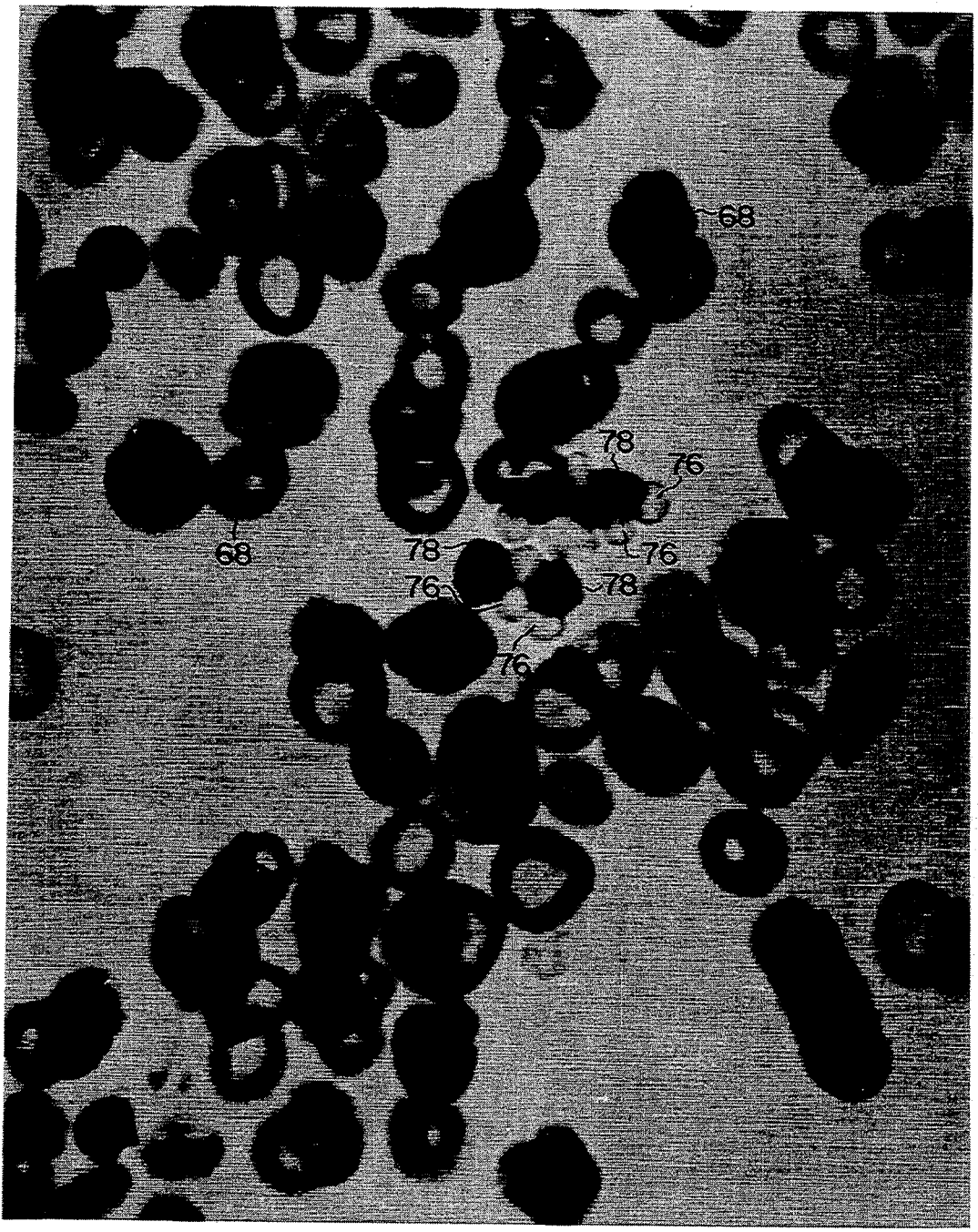
Figure 7:
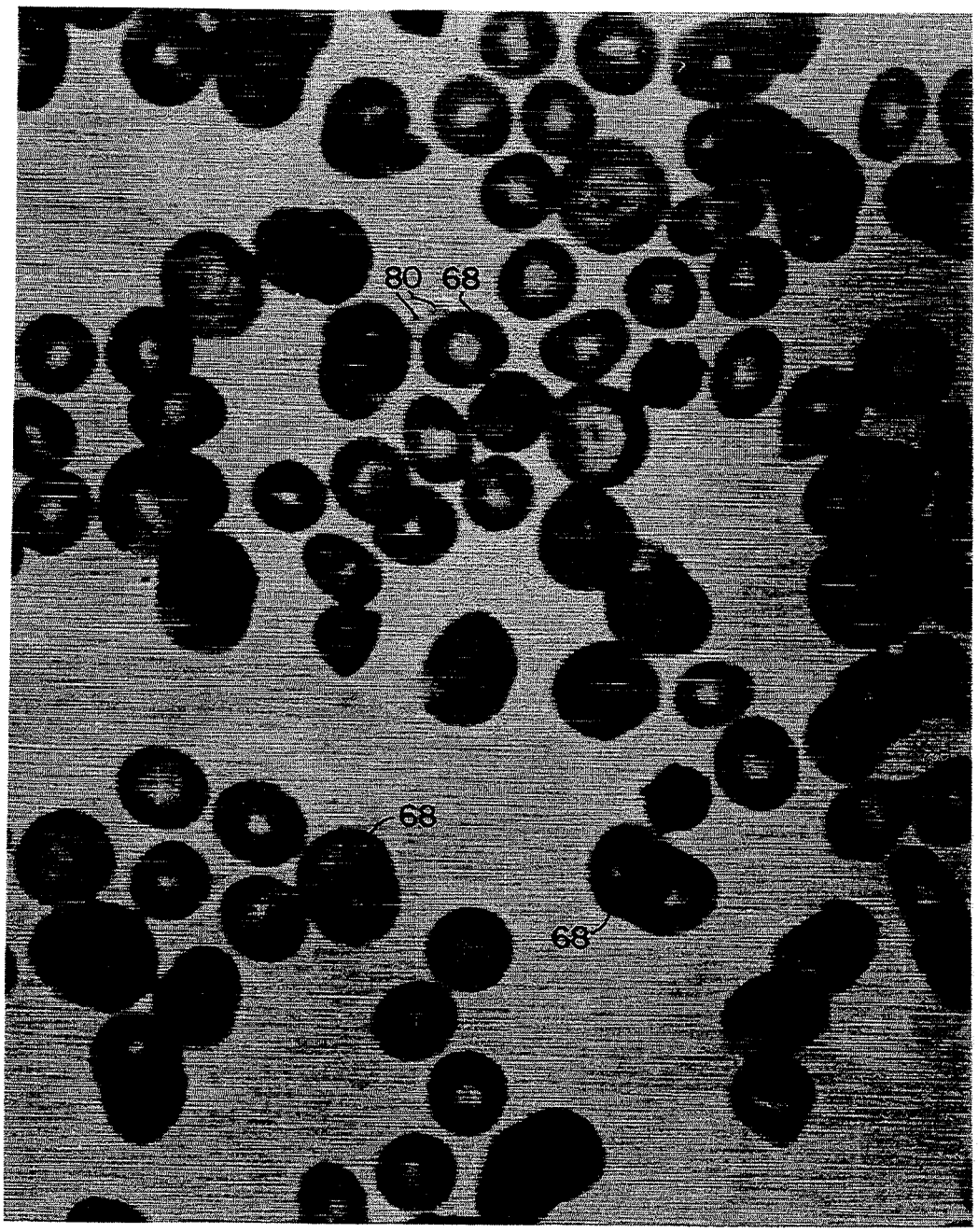

FIG. 6 illustrates a plurality of microspheres 76 having a B1 specific antibody bound thereto bound to lymphocytes 78 which exhibit the presence of B cell CLL. The microspheres 76 are three micron microspheres, whereas the microspheres 64 and 72 are two micron microspheres. This pattern showing a plurality of lymphocytes 78 having microspheres 76 bound thereto is indicative of B cell CLL, since in normal blood very few L's are B1 type lymphocytes.

Referring to FIG. 7, the lymphocytes 78 again were mixed in another sample portion with a plurality of microspheres 80 having a J5 specific antibody bound thereto. The microspheres 80 will bind to some types of CLL and hence the non-binding of the microspheres 80 (two free ones of which are shown adjacent one RBC 68), indicates that the lymphocytes 78 exhibit the absence of CALLA to which J5 does bind.

Figure 8:
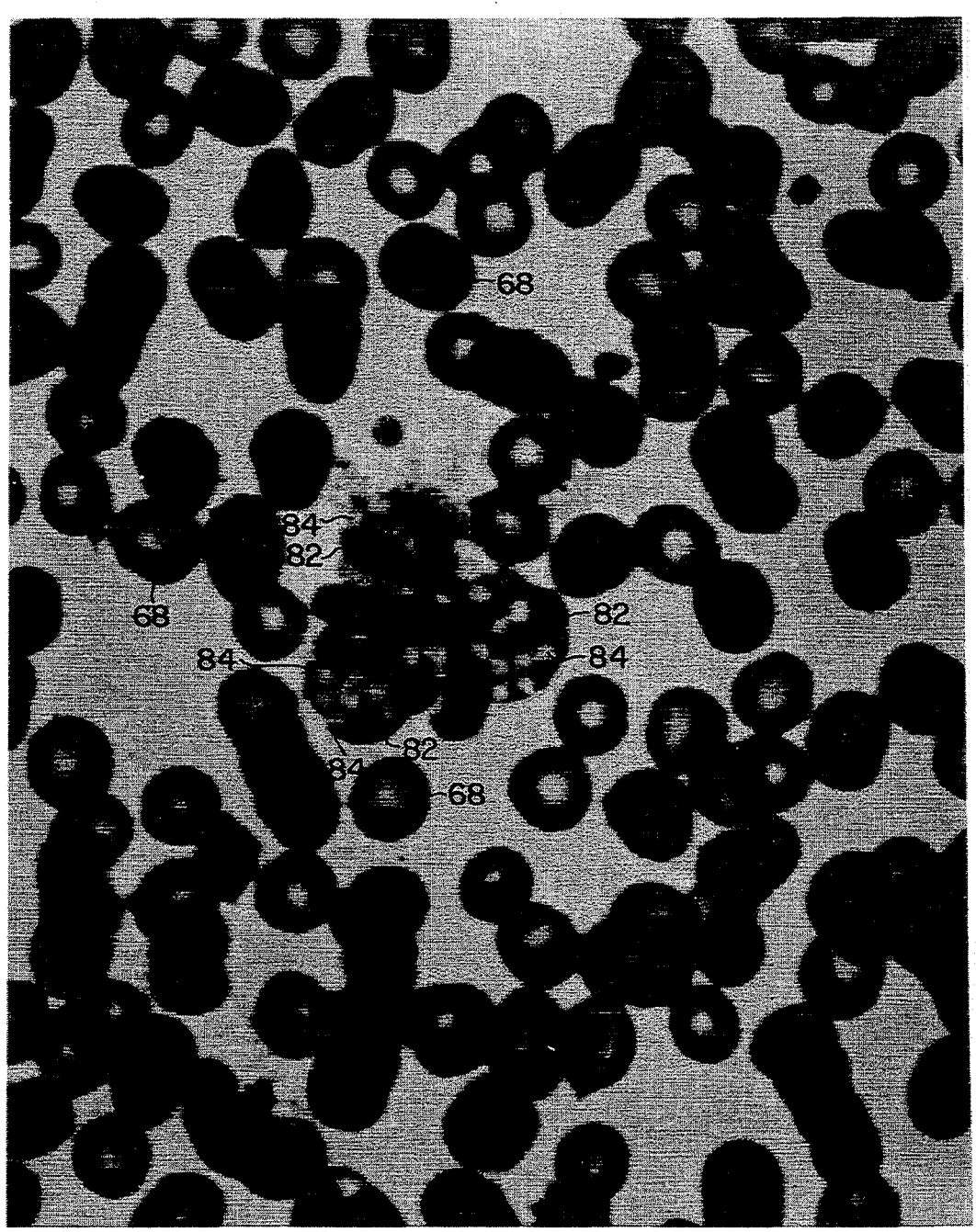

FIG. 8 illustrates three neutrophils 82, each having a plurality of microspheres 84 having an N and E specific antibody bound thereto, such as previously referenced. This illustrates the specificity of the N and E microspheres to the neutrophils 82. In each of the examples, the whole slide or a major portion thereof was traversed to ascertain that the microspheres do not bind to any other WBC's, other than those to which they are specific.

Figure 9:
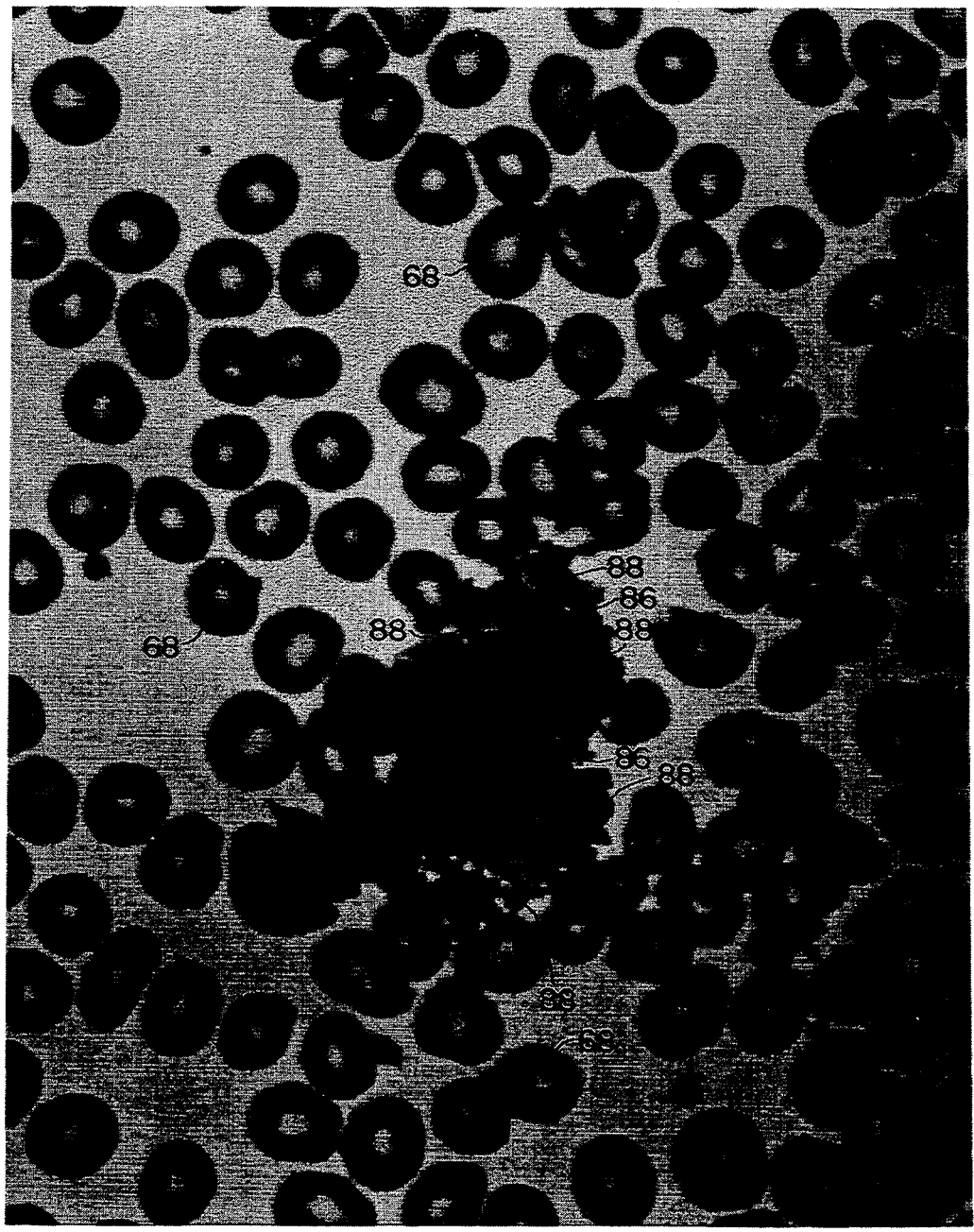

FIG. 9 illustrates two neutrophils 86, each having a plurality of microspheres 88 bound thereto. The microspheres 88 again having an N and E specific antibody bound thereto. In this case, the microspheres are magnetic on the order of one micron diameter and whereas the non-magnetic microspheres appear white in color on the slides, the magnetic microspheres 88 appear brownish in color and can be differentiated in color from the non-magnetic microspheres as well as in size.

Figure 10:
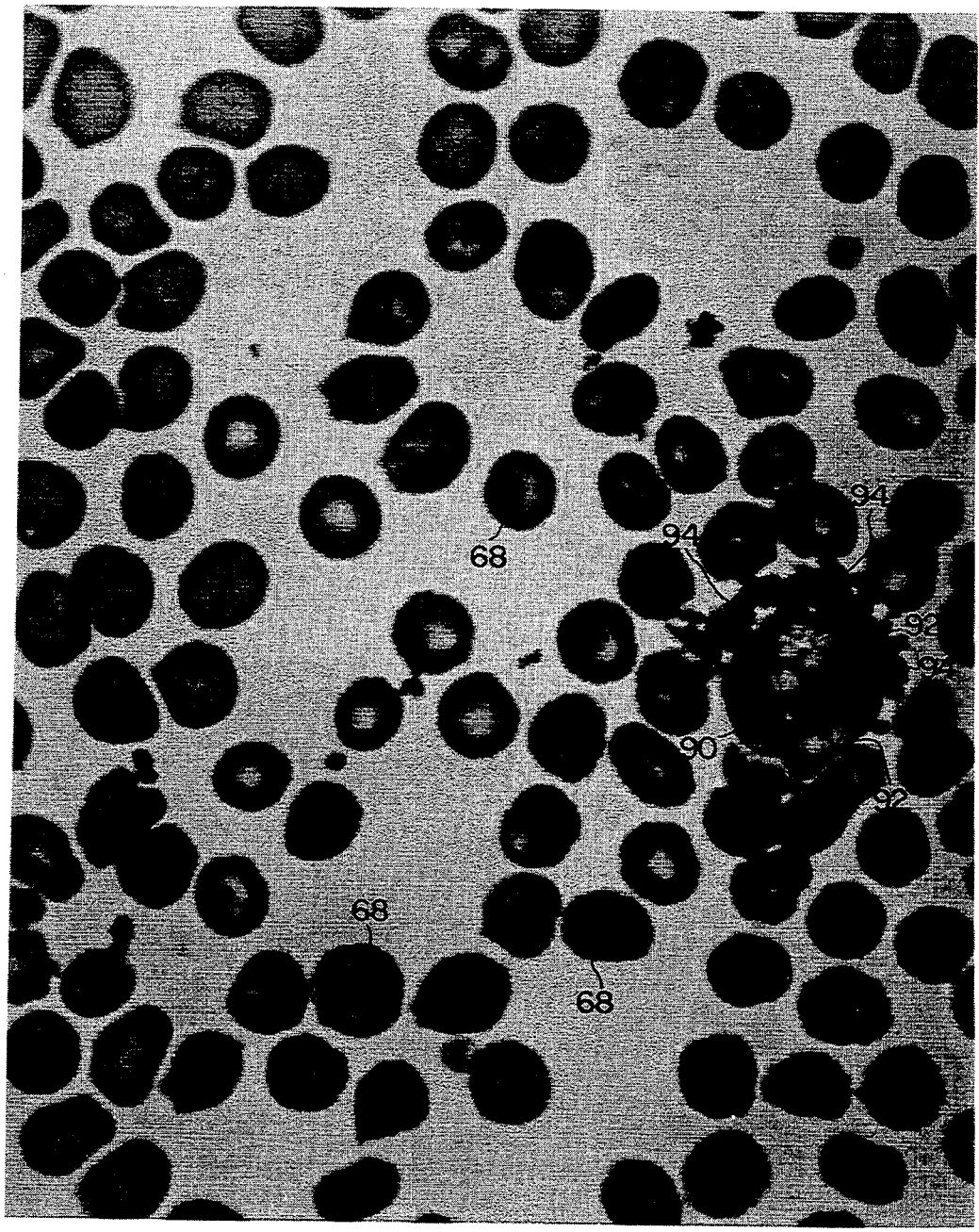

This differentiation is best illustrated in FIG. 10, where a single neutrophil 90 is illustrated having a plurality of two micron non-magnetic white microspheres 92 bound thereto, with the microspheres 92 having an N specific antibody bound thereto, such as previously referenced. The neutrophil 90 also has a plurality of one micron magnetic brownish microspheres 94 bound thereto, with the microspheres 94 having an N and E specific antibody bound thereto. This allows a specific cell to be identified as having two or more antigens of interest simultaneously identified.

The RBC's generally would not be removed as is illustrated in FIGS. 4–10. The smears illustrated in FIGS. 4–10 are prepared in the conventional way of viewing blood cells, with all cells present. Further, cytocentrifugation can damage the cell morphology, especially abnormal cells and hence is not preferred. However, it can be most convenient to remove the RBC's when only a very low WBC count on the order of about 1000–2000 WBC's/ul or less are present. The concentration of the WBC's greatly facilitates their observation. The RBC's should be removed in the least damaging manner so as least to affect the remaining cell morphology.

One preferable manner of removing the RBC's is by adding a lyse to the sample followed by a quench. The lyse preferably can be a mixture of citric acid monohydrate at a concentration of approximately 0.21 percent (w/v) and saponin at a concentration of approximately 0.02 percent (w/v). The quench preferably can be an aqueous solution of sodium chloride at a concentration of approximately 2.9 percent (w/v) and sodium bicarbonate at a concentration of approximately 0.59 percent (w/v). A bacteriostatic agent, for example, sodium azide at a concentration of approximately 0.01 percent (w/v) is recommended, but not required for performance of both the lyse and quench.

In general, utilizing the above lyse and quench, the procedure is as follows:

1. Add 100 ul of EDTA whole blood to a test tube.
2. Add appropriate microsphere volume to the blood, for example 40 ul of microspheres at $2 \times 10^7$/ml.
3. Mix gently for a time sufficient to bind the cells to the microspheres, for example on the order of ten to thirty minutes.
4. Remove 35 ul of the mixture and add to a $12 \times 75$ mm tube.
5. Add 500 ul of the lyse and vortex slightly.
6. Immediately add 250 ul of the quench.
7. Incubate for about one minute.
8. Add buffer of 100 ul, 5 percent BSA in PBS, if desired.
9. Add 400 ul of the mixture in the cytocentrifugation device and spin at 500 rpm for 5 minutes to spin the cells onto the slide.
10. Step 10 is the same as steps 6–8 of the procedure set forth on pages 17 and 18.

The RBC's also can be removed utilizing magnetic microspheres as previously described.

Figure 11:

FIG. 11 illustrates a cytocentrifugation slide which has been depleted of all cells other than the WBC's. The RBC's if present and other cells if desired are removed and then the remaining cells are spun down onto the slide to concentrate the cells and remove excess moisture. This can facilitate the observation of the cells of interest, which can be a relatively small number in a whole blood sample and hence hard to locate. FIG. 11 illustrates a plurality of microspheres 96 having a T11 specific antibody bound thereto, which microspheres 96 are bound to three lymphocytes 98. The microspheres 96 are not bound to a neutrophil 100 or a monocyte 102, which were also exposed to the microspheres 96.

Figure 12:
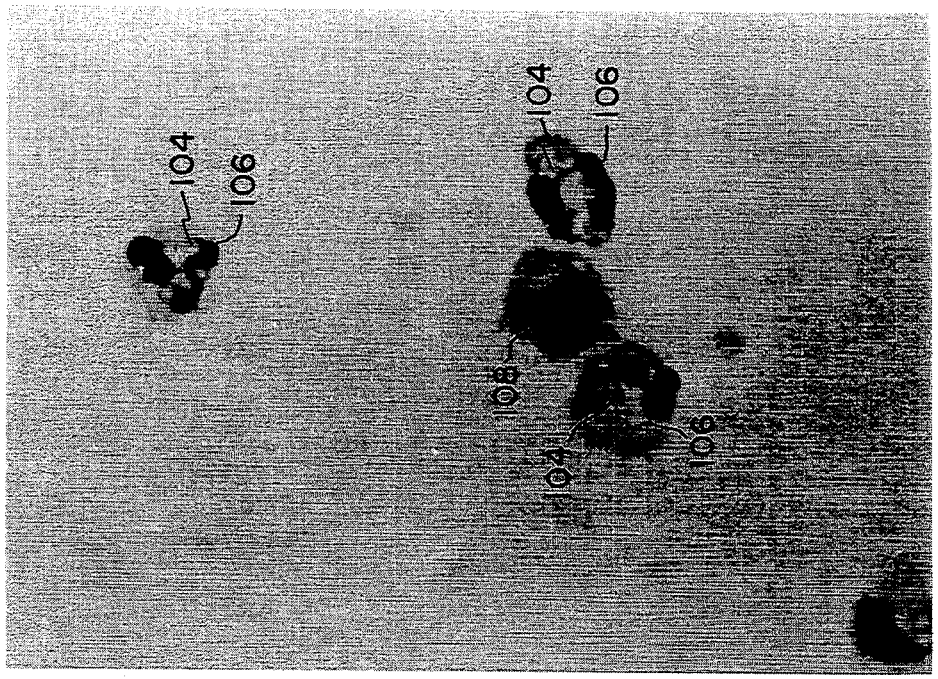

FIG. 12 is another cytocentrifugation prepared slide, which illustrates a plurality of microspheres 104 having an N and E specific antibody bound thereto, which microspheres 104 are bound to several neutrophils 106 and are not bound to a monocyte 108.

Although specific examples have been illustrated utilizing microspheres which are differentiated by size and color, the microspheres also can be differentiated by being of different shapes.

Two further phenomena have been observed in practicing the present invention. These are rimming and slide agglutinations, which both can be called cell clumping. Rimming occurs in some whole blood samples with a high number of cells positive for a specific antigen. The phenomena has been observed during the mixing or incubation period of the whole blood with the microspheres in a reaction vessel, such as a test tube. The positive cells and microspheres tend to aggregate along the outer surface of the whole blood forming a macroscopic rim on the test tube. This rim is only seen in samples which are positive. A similar agglutination phenomena has also been observed on a microscopic glass slide. By placing a drop of whole blood on the slide and mixing it with a drop of antibody-coated latex beads by gently rocking the slide, a macroscopic agglutination can be seen in samples with a high number of cells positive for that specific corresponding antigen. This agglutination appears as white clumps with the red blood background on the slide, visual to the naked eye.

These agglutinations can provide a fast screening procedure for high WBC counts under appropriate conditions. These phenomena have been observed with total WBC cell counts on the order of 40–50,000 cells or greater per microliter as contrasted to a normal WBC cell range of 4–11,000 cells per microliter. Although the cell clumping can be visually observed without aid, a microscopic instrument operated manually or automatically or other optical device, can be utilized. Further, rimming can be visually observed manually or automatically optically by scanning the mixing vessel with a light beam which will cause a diffraction pattern when rimming occurs.

Figure 13:
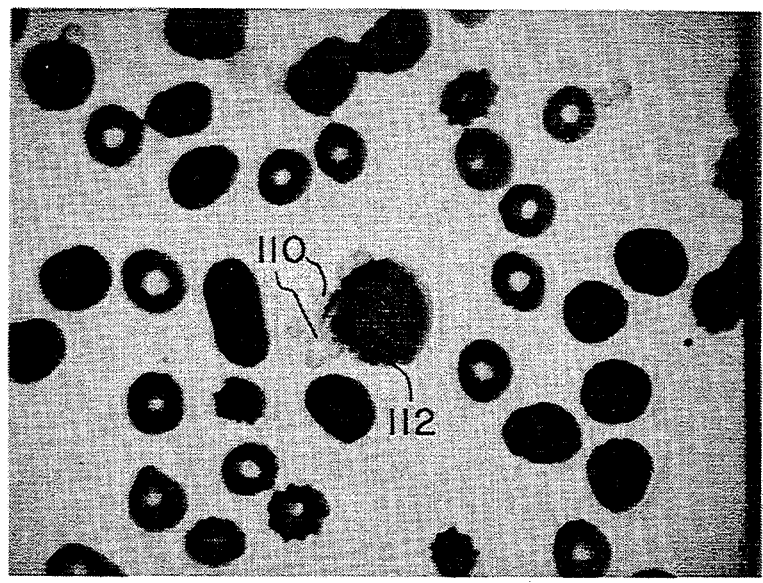

FIG. 13 illustrates a plurality of microspheres 110 having a second reactant bound thereto, which second reactant binds to a first reactant, which first reactant in turn binds to a specific molecule on a cell 112. In this case the cell expresses the CD34 antigen, which the first reactant binds to. The first reactant, for example HPCA-1, is not readily available in the proper concentration to be bound directly to the microsphere 110. Therefore, a second reactant, here a goat anti-mouse antibody, is bound to the microspheres. The second reactant will bind to any mouse antibody and thus the microspheres 110 will bind to the first reactant bound to the microspheres on the cells 112. The first reactant and microsphere 110 bound to the second reactant also could be combined with the sample simultaneously. Alternatively, the first reactant could be bound to the second reactant on the microspheres 110 and then the microspheres 110 with the second reactant bound thereto and the first reactant bound also thereto via the first reactant then can be combined with the sample. The first reactant bound to the cell 112 alone, without the microspheres 110, is not visually or microscopically differentiable.

In general, the first procedure is as follows:

1. Step 1 is the same as steps 1 and 2 of the previous procedure set forth on pages 17 and 18.
2. Add 10 ul of the first reactant and vortex mixture for approximately 2–3 seconds.
3. Incubate mixture for about 10 minutes.
4. Add 10 ul of microspheres with the second reactant bound thereto.
5. Step 5 is the same as steps 4–8 of the procedure set forth on pages 16 and 17.

The other types of procedures illustrated with respect to FIGS. 5–12, can also be utilized with the type of reactant binding described with respect to FIG. 13. Other sets of microspheres with different reactants can be added to a second sample portion, the microspheres being of different sizes and/or colors to be differentiated therebetween. One or more different sets of microspheres with different reactants also can be combined with the first and second reactants in the first sample portion. In this procedure, however, the other reactants must be of a different type than the second reactant, otherwise the microspheres also will bind to the second reactant. For example where the second reactant is an anti-mouse antibody, the other reactants could be a swine, rabbit or other different antibody type.

Different procedures as described with respect to FIG. 13 were attempted to ascertain the effects of the various methods. As a first example, 5 ul of T4 antibody were added to 100 ul of whole blood by gently vortexing. The mixture was left to stand or incubate for 10 minutes. After incubation, 10 ul of microspheres were added, vortexed gently and mixed on a roller rocker for 10 minutes, after which a smear was made as above described. This resulted in the usual binding of the microspheres to the L's, two examples being 37 and 44 percent.

In a second example the microspheres and T4 antibody were added at the same time and roller rocked for 10 minutes before preparing a slide. This resulted in a somewhat decreased percentage of 28 and 31, for two examples.

As a third example, the microspheres were added and mixed without any antibody, before mixing and making the slide. In this example, as expected, no binding of the microspheres to the cells was found.

In another example, the T4 antibody was roller rocked for 10 minutes with the sample, then the microspheres were added and also mixed for 10 minutes, then the slide was prepared. This resulted in a normal percent of 36.

As a final example, the microspheres and T4 antibody were mixed together and left to stand for 10 minutes. This mixture then was added to the sample portion and mixed 10 minutes prior to preparing the slide. The percent obtained 23 and 27 were somewhat lower. One explanation is that some of the antibody remained free in the mixture and blocked some of the sites to which the microspheres would have bound.

Figure 14:
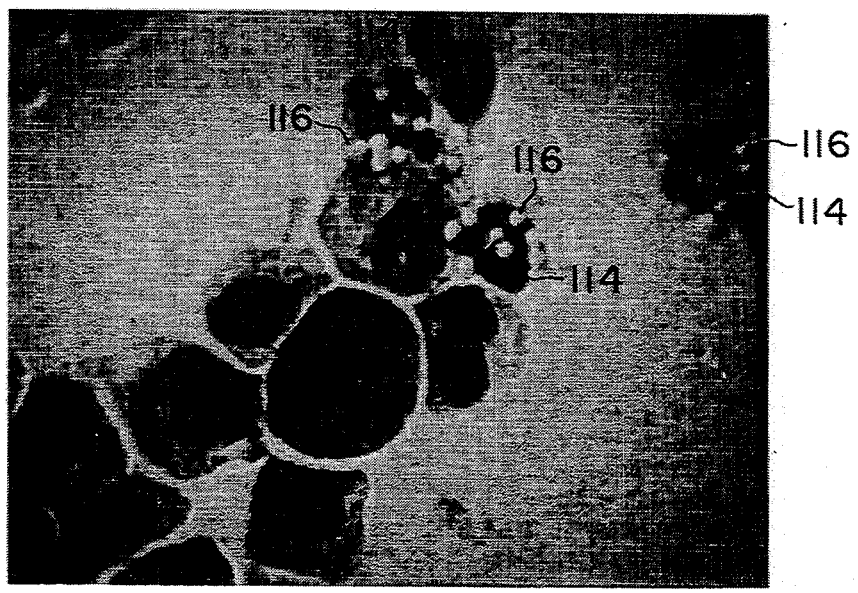

FIG. 14 illustrates several neutrophils 114 in a bone marrow sample, each having a plurality of microspheres 116 bound thereto. The microspheres 116 have an N specific antibody bound thereto. This example illustrates the effectiveness of the procedure in other types of fluids other than blood, here bone marrow.

Referring now to FIGS. 15–18, the embodiments of the present invention are illustrated.

Figure 15:
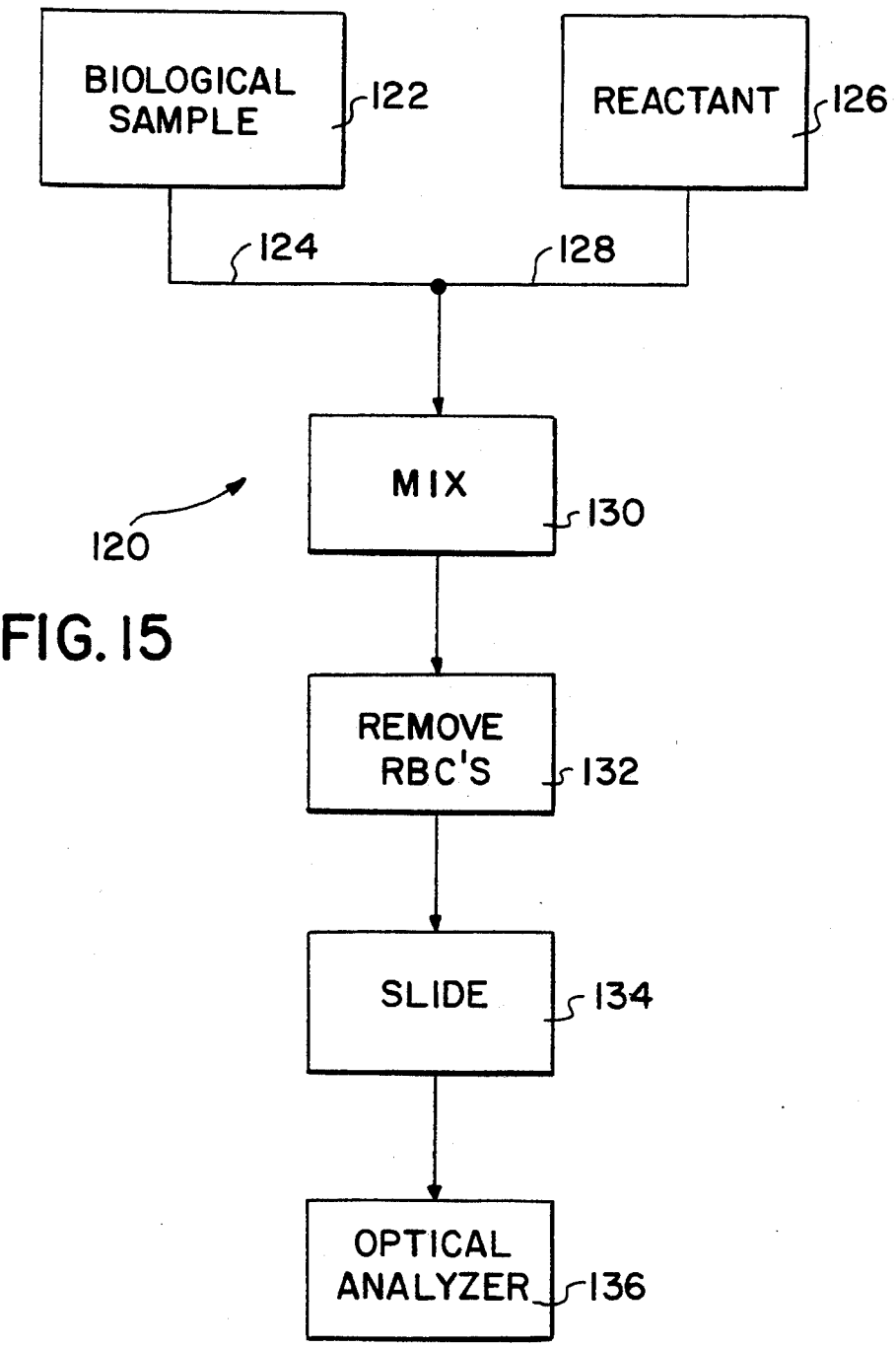
FIGS. 15–18 describe the embodiments of the present invention.

Referring to FIG. 15, a first optical cell counting embodiment of the present invention is designated generally by the reference character 120. The optical cell counter 120 includes a biological sample 122, which contains at least a first set of biological cells (not illustrated), such as in or from a whole blood sample.

The sample 122 is combined via a line 124 with at least one reactant 126 via a line 128. The reactant 126 can include a chelating agent, such as standard EDTA added to the sample 122 as a blood anticoagulating agent and to prevent the neutrophils (N's) from ingesting the microspheres.

The reactant 126 also includes a plurality or a first set of microspheres, having an antibody specific to a particular antigen which can exist on at least one type of cell bound thereto. For blood, the cells express antigens to which a specific antibody or antibodies will bind. In general, antigens are molecules as are the antibodies which will bind thereto, and therefor for blood or other viable cells, the reaction can be specified as a first type of molecule which chemically interacts specifically with a second type of molecule. The combined sample 122 and the reactant 126 then preferably are mixed in a functionally designated mixing station 130.

A specific volume of the mixture of the biological sample 122 and the reactant 126 then is mixed with a specific volume of a lysing agent to remove the RBC's in a RBC removal station 132. The specific volume of sample mixture and lysing agent can be mixed manually or automatically, such as disclosed in the above-referenced application Ser. No. 517,309.

The lysed mixture then is placed on a slide 134, without quenching. The slide 134 can be a hemacytometer which divides the lysed mixture into a known volume divided among a number of chambers (see FIG. 16). The slide 134 then is optically viewed in an optical analyzer 136, such as a conventional light microscope. The cells of interest which have the microspheres bound thereto, are counted in a plurality or all of the chambers and then related to the known sample volume to obtain an absolute cell count. Without the microspheres bound thereto, the optical viewing of the cells does not allow the various cell subsets to be identified. For example, a CD4 positive L looks exactly the same as a CD4 negative L. Therefor without the selective attachment of the microspheres with the specific monoclonal antibody bound thereto, no subset differentiation optically can be made.

The absolute cell count can be for any desired cell population or subset population, such as one or more WBC subset populations, which can be distinguished by binding of one or more antibodies bound to microspheres specifically thereto. For example, in AIDS patients, the absolute cell count of the CD4 cell population is important for diagnostic and treatment purposes. If the blood is suspected as having the AIDS virus, then a fixative would be added to the sample mixture to kill the virus such as in the station 132, for example such a fixative can be paraformaldehyde.

Further, a second set of microspheres physically or optically different from the first set of microspheres also can be added into the sample mixture. For example, in obtaining a CD4 absolute cell count, the CD4 antigen exists on both L's and M's. If the first set of microspheres are titrated correctly, then the M's will not have the microspheres bound thereto. The titration procedure may be utilized where the desired population, here L's, has a greater or higher affinity than the secondary or non-desired population, as for example with the M's. However, in practice this could be very difficult to reliably depend upon. To ensure that M's are not counted, the second set of microspheres first can be added with a monoclonal antibody specific only to the M's, for example CD14, to block the counting of the T4 positive M's as incorrect T4 positive L's. The two sets of microspheres can be different, for example, in size, shape or color to be easily optically differentiated from one another.

Figure 16A:
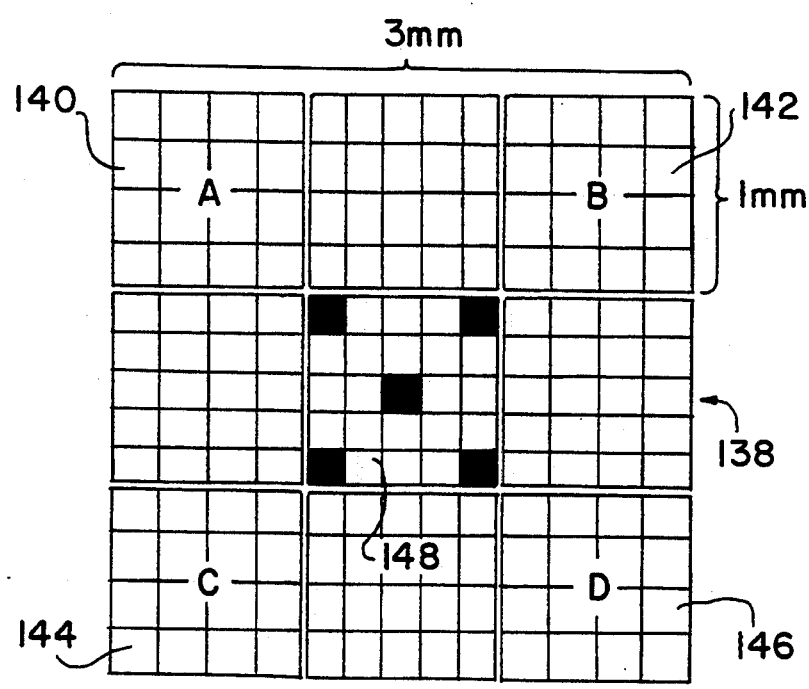
FIGS. 16A and B respectively are top and cross-sectional side views of a typical hemacytometer chamber.
Figure 16B:
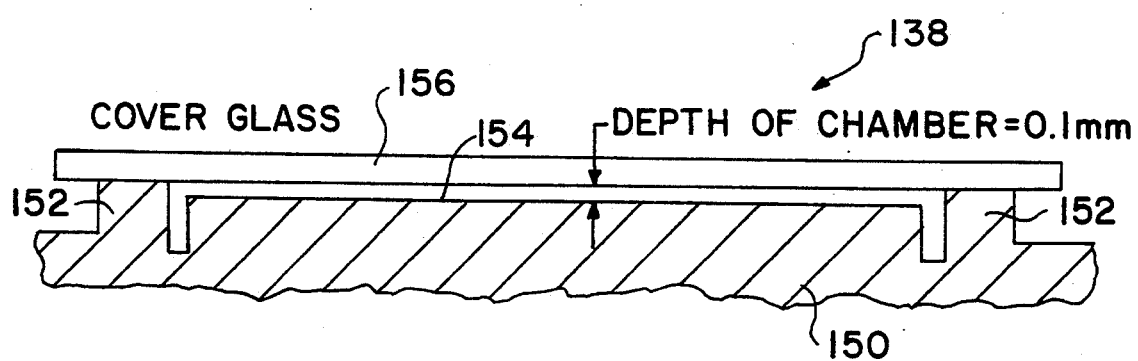

Referring to FIGS. 16A and 16B, a conventional hemacytometer chamber 138 is best illustrated, which can form the counting chamber for the slide 134. In a conventional cell count, there can be nine grids or subsections, however only the corner subsections 140-46 are utilized to count WBC's, while a central subsection 148 is utilized to count RBC's and/or platelets. The chamber 138 typically is formed in duplicate on the slide 134 and includes an overflow well and loading groove (not illustrated).

The chamber 138 includes a base 150 (FIG. 16B) formed of an optically clear material, such as glass or plastic, which includes a plurality of side walls 152 defining a central area 154 onto which are formed the nine grids, including the grids or subsections 140-148. The slide 134 is completed by placing a glass cover 156 on top of the walls 152 after which the sample to be counted will be loaded.

In general, to obtain an absolute cell count in accordance with the present invention, the procedure is as follows:

1. Add well mixed whole blood to an EDTA tube if not collected in EDTA. It is preferred that the blood be collected in EDTA.

2. Add 100 ul of the blood from the EDTA tube to a test tube.

3. If a WBC subset is being counted which has an antibody specific only to the WBC subset, then the antibody bound microspheres are added and mixed with the sample mixture for about two (2) minutes. Preferably, if a WBC subset is to be blocked, for example, the M's are to be blocked, then the MY4 bound microspheres first are added and mixed with the mixture for about two (2) minutes. Then the T4 or other WBC subset antibody bound microspheres are added and mixed with the mixture for about an additional two (2) minutes.

4. Add a specific volume of the sample and microsphere mixture with a specific volume of the lyse, such as two (2) percent acetic acid in a dilution one (1) to ten (10). For example, utilize ten (10) ul of the sample mixture combined with ninety (90) ul of acid.

5. Mix (manually or automatically) for a time period on the order of up to ten (10) seconds.

6. Load the hemacytometer with a specific volume of the lysed sample mixture, precisely diluted, such as utilizing a UNOPETTE, manufactured by Bector-Dickinson of Rutherford, N.J. The sample mixture volume added to the hemacytometer is sufficient to fill the chamber, without overflowing.

7. Optically view the cells in one or more grids and count the cells with the microspheres attached to obtain a cell count related to the specific volume and correct to obtain an absolute cell count. The dilution from the original blood sample determines the multiplier to obtain the required cell count.

The cells can be counted utilizing a suitable light microscope with a suitable lens, for example, a 40 x objective. The procedure can include, if necessary, the addition after or during step 6 of a suitable fixative to ensure that the HIV (AIDS) virus is killed. A suitable fixative can be paraformaldehyde.

The term "absolute cell count" as utilized herein, is a count per unit volume, in this example, one (1) microliter of the whole blood sample. The dilutions are factored out of the final count.

Some additional steps must be taken if an absolute CD4 cell count is to be obtained. As above mentioned the M's also include the CD4 antigen. The M's as above mentioned can be eliminated by proper titration so that the microspheres do not attach to the M's, by the number of microspheres on the M's or by marking the M's with a second set of microspheres having an M specific antibody bound thereto and which microspheres can be differentiated in size, color or shape from the CD4 microspheres.

Also although in a standard hemacytometer cell count, only some of the grids or subsections 140-148 of the hemacytometer chamber 138, would be utilized, the CD4 count may be too low to utilize that technique. This is especially true in the case of AIDS samples. In a normal blood sample, there are approximately 5000 WBC's per microliter. If all nine grids are counted, then one tenth (0.1) microliter of sample will be counted or about 500 WBC's (about 55 WBC's per grid or subsection). Of the 5000 WBC's per microliter, only about 1500 are L's of which about 800 are T4 positive. This means for a normal blood sample there are about 80 T4 positive cells in the total grid or about 8 T4 positive cells per subsection.

In an AIDS sample the T4 positive cells can be on the order of 400 or less per microliter and hence only about 40 or less per the whole hemacytometer 138 and 4 or less per each subsection. Although only one chamber 138 is illustrated in FIGS. 16A and 16B, a typical hemacytometer includes a pair of the chambers 138. To address this small number, both of the double chambers are counted for a volume of two tenths (0.2) of a microliter, i.e. doubling the cell count. Also the hemacytometer 138 well(s) can be made deeper to also further increase the volume counted. The shoulders or walls 152 can be made as high as possible while still allowing the cells to settle and be counted, for example, two (2) to four (4) times higher again multiplying the volume counted to enhance the low total count.

A further and desirable but optional step is to stain the cells on the slide, which enhances the distinguishability of the cells and hence also enhances obtaining the desired count. The stain can be, for example, Gentian or Crystal Violet at a dilution of 0.025% in the acetic acid, preferably incorporated with the lyse. The stain could be separate if desired.

A prior art general or reference procedure also was established to provide a check against the procedure above referenced, which for purposes herein was a manual procedure. The reference procedure is:

1. Obtain a sample of EDTA whole blood.
2. Determine the total WBC count and differential using, for example, a Coulter STKS instrument.
3. Determine the percent of lymphocytes which are T4 positive.
   a. Transfer 100 ul of whole blood to a 12×75 mm test tube.
   b. Add 10 ul of Coulter Cyto-stat T4RD1/T8F-ITC (two color) reagent and vortex to mix.
   c. Incubate the mixture for 5–10 minutes.
   d. Lyse, quench and fix the T4RDI/T8FITC labeled sample using a Coulter Q-prep.
   e. Analyze the stained sample on a Coulter Profile, using the bit map gate to enclose the lymphocyte population.
4. Calculate from the above data the absolute T4 lymphocyte count:
   WBC count x % Lymphocytes x % T4+ Lymphocytes.

Comparative results of the above named method and the reference method are disclosed respectively in Tables II and III, with the M's blocked as above described when counting CD4, utilizing in this example T4 as the specific antibody, as follows:

TABLE II

| SAMPLE IDENTIFICATION | T4CT | AVG | SD | % CV | T8CT | AVG | SD | % CV |
|---|---|---|---|---|---|---|---|---|
| 47148-1 | 980 | 847.00 | 115.97 | 13.69 | 660 | 653.67 | 6.51 | 1.00 |
| 47148-2 | 794 | | | | 647 | | | |
| 47148-3 | 767 | | | | 654 | | | |
| 28522-1 | 980 | 1020.33 | 75.12 | 7.36 | 460 | 522.33 | 119.40 | 22.86 |
| 28522-2 | 1107 | | | | 660 | | | |
| 28522-3 | 974 | | | | 447 | | | |
| 46186-1 | 754 | 698.00 | 49.52 | 7.09 | 554 | 551.67 | 16.62 | 3.01 |
| 46186-2 | 660 | | | | 534 | | | |
| 46186-3 | 680 | | | | 567 | | | |

TABLE III

| SAMPLE IDENTIFICATION | T4CT | AVG | SD | % CV | T8CT | AVG | SD | % CV |
|---|---|---|---|---|---|---|---|---|
| 47148-1 | 790 | 783.67 | 19.30 | 2.46 | 456 | 446.33 | 15.04 | 3.37 |
| 47148-2 | 762 | | | | 454 | | | |
| 47148-3 | 799 | | | | 429 | | | |
| 28522-1 | 886 | 861.00 | 26.63 | 3.09 | 544 | 522.67 | 25.79 | 4.94 |
| 28522-2 | 864 | | | | 530 | | | |
| 28522-3 | 833 | | | | 494 | | | |
| 46186-1 | 951 | 945.33 | 9.81 | 1.04 | 471 | 467.67 | 4.93 | 1.05 |
| 46186-2 | 934 | | | | 470 | | | |
| 46186-3 | 951 | | | | 462 | | | |

In Tables II and III, CT equals count, AVG equals average, SD equals standard deviation and CV equals SD/AVG.

Table IV illustrates the difference in the CD4 positive counts, with and without blocking or gating of the M's.

TABLE IV

| SAMPLE IDENTIFI-CATION | T4 Count (Unblocked) | | T4 Count Blocked | |
|---|---|---|---|---|
| | T4 Ct. | Reference T4 Ct. | T4 Ct. | Reference T4 Ct. |
| 28522 | 1010 | 1140 | 860 | 710 |
| 29968 | 1650 | 1999 | 1310 | 1450 |
| 49666 | 1200 | 1330 | 1000 | 960 |

Another procedure of obtaining the absolute count is to utilize the stained slide technique of the parent application to normalize an unblocked CD4 count. The CD4 count is obtained by counting all CD4 positive cells in accordance with the present invention without blocking the M's. Then optically identifying on a separate slide smear (since the parent application stain is a histological stain which optically differentiates the type of cells, such as L's and M's) the number of T4 positive L's and T4 positive M's. The ratio of T4 L's/T4 M's, then can be utilized to correct the count of T4 positive cells obtained with the unblocked M sample technique in accordance with the present invention.

Further, the absolute count can be obtained directly if either the cells which should not be counted, but which could be labelled by the same monoclonal antibody can be removed without any nonspecific removal of cells or if the cells removed are consistently the same percentage (number) of the cells removed. This would result in a direct count.

Figure 17:
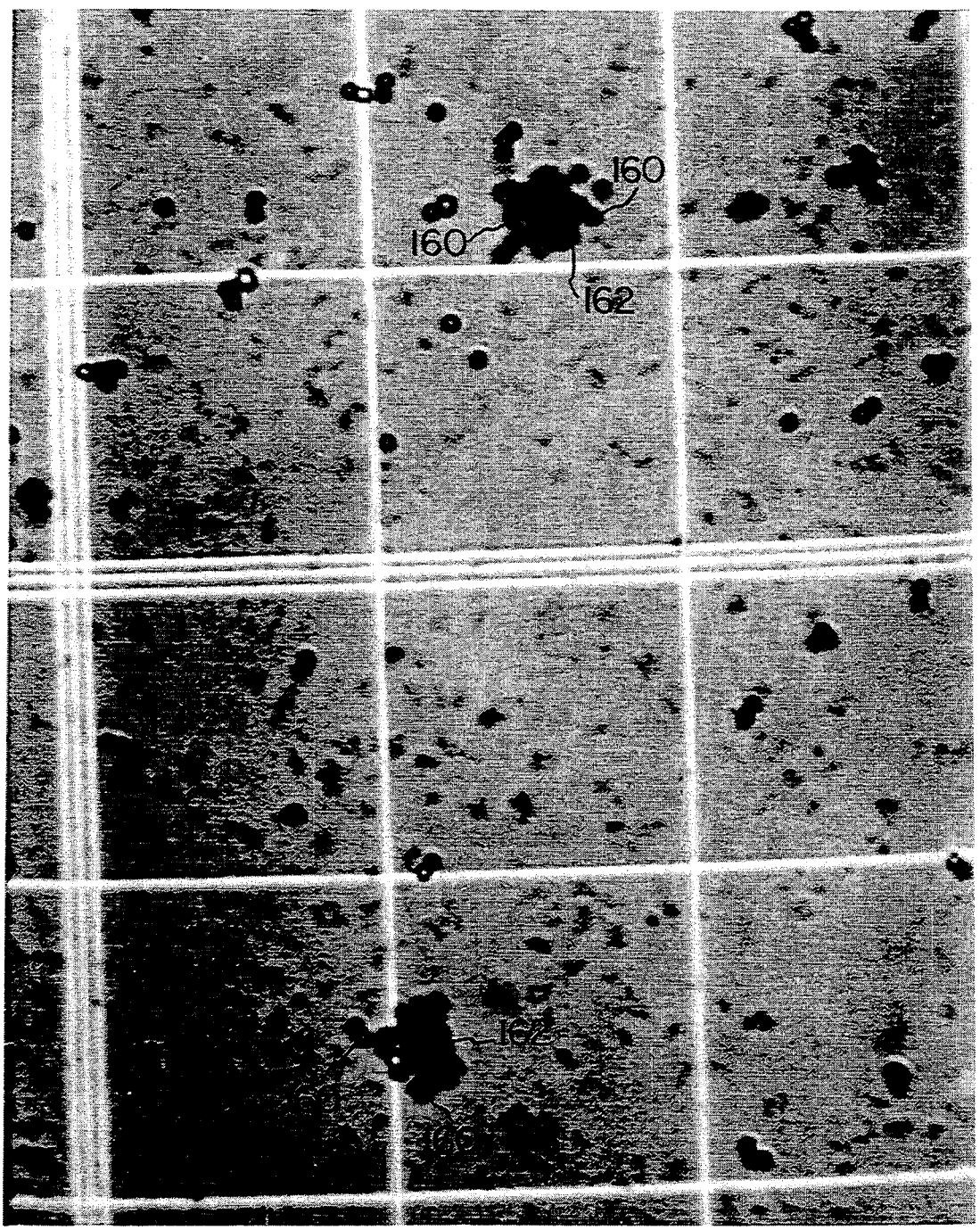
Figure 18:

FIG. 17 illustrates a plurality of non-magnetic microspheres 160 having a CD8 specific antibody bound thereto bound to L's 162. This illustrates an example of an antigen which only binds to the cells of interest, here L's 162. A CD8 negative or untagged cell 164 also is illustrated. On the parent application slides, the cells are flattened out and hence can be differentiated by the morphology with the histological stain utilized. In the present invention, the slides depicted in FIGS. 17 and 18, show cells in fluid in three dimensions. The stain only facilitates differentiation between the background of the cells and the microspheres. The slide, cells and microspheres are various shades of a light pinkish or purple color. Hence, on the slides of the present invention, the cells cannot in general be differentiated between even types of cells, such as L's and M's. Therefor, the microspheres have to be utilized to differentiate the cells and the cell subsets (which subsets also cannot be differentiated utilizing the parent application techniques).

Referring to FIG. 18, a plurality of non-magnetic microspheres 170 having a CD4 specific antibody bound thereto are bound to L's 162. However, in this case since the CD4 specific antibody also will bind to M's CD4, which would produce an erroneous CD4 L subset count, a second set or plurality of non-magnetic microspheres 172 having a CD14 specific antibody bound thereto are first bound to M's 174 to block the binding of the CD4 specific antibody microspheres therefrom. A pair of CD4 and CD14 negative or untagged cells 176 and 178 also are illustrated. In FIGS. 17 and 18, the microspheres 160 and 170 are both two (2) micron microspheres. In FIG. 17, the microspheres 170 and 172 have to be optically differentiated, since the cells cannot be optically differentiated; therefor, the microspheres 172 are one-half (0.5) micron microspheres. In the case of the L's 162 and M's 174, once the microspheres are bound thereto, the cell itself is partially or totally obscured. Also, although not shown in FIG. 17, the microspheres 172 do not always block all of the CD14 antigens and hence the M's 174 also can bind both the microspheres 170 and 172 thereto.

The above-referenced examples in tables II, III and IV and the other examples (FIGS. 17 and 18) herein are from so-called normal blood samples (i.e. non-AIDS/-non diseased). A few AIDS samples have been analyzed in accordance with the present invention and absolute T4 counts of substantially less than 400 clearly appear obtainable. Hence, the methodology of the present invention also appears to be equally effective for diseased blood samples, such as AIDS.

While the present invention is primarily directed at obtaining one or more absolute WBC subset counts, the present invention also can obtain a multipart WBC differential/absolute count. In this case, one or several portions of the blood sample are treated as above described, with each sample obtaining one or more counts. The individual cell counts then are compared to obtain a multipart differential/absolute count. For example, a four part WBC differential/absolute count can be obtained from a whole blood sample as follows:

1. Add CD14 specific antibody (such as MY4) bound microspheres to a first sample portion to obtain a M count.
2. Add N specific antibody (such as 1D3) bound microspheres to a second sample portion to obtain a N count.
3. Add either a E specific antibody or an N and E specific antibody (such as KC-48) bound microspheres to a third sample portion to obtain an E count directly or by subtracting the N count from the N and E count.
4. Count the total WBC's in one of the sample portions or a fourth sample portion and subtract from the total the number of M's, N's and E's from the above counts to obtain the L count (actually the L's plus B's).

Although the example utilized three (3) or four (4) sample portions, it is possible to combine optically different sets of microspheres to accomplish the differential/absolute count in two (2) sample portions. For example, the N and M counts could be performed in one sample portion, with the respective N and M sets of microspheres being optically different in size, shape and/or color. Potentially, all of the counts could be performed in a single sample portion. Further, the B's typically are fairly insignificant, totally less than one (1) percent of the WBC's. A suitable L or B specific antibody would allow a full five-part WBC differential/absolute count to be obtained.

The prior art slide/blood smear techniques allow a five part differential to be obtained by optically determining and counting the different M's, N's, L's, E's and B's through a microscope on the smear. This, however, requires a technician trained in cell morphology and even then there are difficulties on occasion making a determination between some cells. Further, an automated instrument utilizing an image analyzer, may well not be able to distinguish between some cells. Also, absolute counts cannot be obtained utilizing the smear technique. In the present invention, the absolute subset cell count is obtained and an absolute differential count of the M's, N's and E's is obtained and the L's (including B's) then are calculated from the total WBC's. Since only a count must be obtained of those cells to which microspheres (or different microspheres) are attached, without regard to cell morphology, an image analyzer or unskilled technician more easily can obtain the required counts.

We claim as our invention:

1. A method of optically screening and counting microscopic cells, comprising:

providing a complete whole blood sample with an anticoagulating agent or a portion thereof including a plurality of cells and including at least one WBC population;

combining at least a first portion of said cells with at least a first set of microspheres having at least a first reactant bound thereto specific to at least a first specific molecule which can exist on at least one type of cell to form a sample mixture, said first reactant being a CD4 specific molecule antibody specific to at least said first specific molecule which is a first cell antigen;

combining said first portion of said cells with at least a second set of microspheres having at least a second CD14 antibody bound thereto specific to at least a second specific antigen which can exist on at least one type of cell, said second set of microspheres having a different optical characteristic from said first set of microspheres;

deleting the RBC population from said sample prior to forming said sample mixture on a slide;

forming a specific volume of said sample mixture on a slide;

optically viewing at least some of said cells with a microscope to at least identify and count at least the presence of cells to which said first set of microspheres are bound including said cells to which said CD4 microspheres are bound and obtaining a CD4 absolute count and to at least identify the presence or absence of cells to which said second set of microspheres are bound; and relating said cell count to said specific volume to obtain an absolute CD4 cell count.

2. The method as defined in claim 1 including adding a chelating agent to said sample to prevent the neutrophil population from ingesting said microspheres.

3. The method as defined in claim 1 including concurrently combining said first portion of said cells with at least said first and second set of microspheres.

4. The method as defined in claim 1 wherein said first and second set of said microspheres are physically different in size.

5. The method as defined in claim 1 wherein first and second set of said microspheres are optically different in color.

6. The method as defined in claim 1 including adding said first and second set of microspheres sequentially.

7. The method as defined in claim 6 including adding said second set of microspheres first.

8. The method as defined in claim 1 including mixing said first portion of said cells with said first and second set of microspheres.

9. The method as defined in claim 1 including deleting said CD14 cells to which said second antibody is bound prior to optically viewing said cells.

10. The method as defined in claim 1 including staining the cells in said cell mixture on said slide to optically enhance the differentiation of said cells.

11. The method as defined in claim 1 including providing a hemacytometer and forming said specific volume on said hemacytometer.

12. The method as defined in claim 1 including diluting said whole blood sample.

13. The method as defined in claim 1 including deleting said RBC population by lysing said RBC population and including said lyse in said specific volume.

14. A kit for performing an absolute CD4 count on a whole blood sample on a hemacytometer, said kit comprising:

a first set of CD4 microspheres having at least a CD4 antibody bound thereto specific to CD4 antigen present in WBC populations, such as lymphocyte cells and monocyte cells;

a second set of monocyte blocking microspheres having at least a CD14 antibody bound thereto specific to a monocyte antigen which exists on monocyte cells, said monocyte blocking microspheres having a different optical characteristic from said CD4 microspheres which will optically distinguish said monocyte CD4 cells from said lymphocyte CD4 cells; and a reactant for deleting the RBC population prior to forming a specific volume of a sample of the hemacytometer.

15. The kit as defined in claim 14 wherein said CD4 microspheres are physically different in size than said monocyte blocking microspheres.

16. The kit as defined in claim 14 wherein said RBC reactant is an RBC lyse.

17. The kit as defined in claim 16 wherein said RBC lyse includes acetic acid.

18. The kit as defined in claim 14 further including a cell stain.

19. The kit as defined in claim 18 including said cell stain in said RBC reactant.

20. The kit as defined in claim 14 further including a hemacytometer.

* * * * *